(12) United States Patent
Betts et al.

(10) Patent No.: US 6,495,551 B1
(45) Date of Patent: Dec. 17, 2002

(54) SUBSTITUTED PHENYLOXAZOLIDINONES AND THEIR USE AS ANTIBIOTICS

(76) Inventors: Michael John Betts, Alderley Park, Macclesfield, Cheshire, SK10 4TG (GB); Michael Lingard Swain, Alderley Park, Macclesfield, Cheshire, SK10 4TG (GB)

( * ) Notice: Subject to any disclaimer, the term of this patent is extended or adjusted under 35 U.S.C. 154(b) by 0 days.

(21) Appl. No.: 09/555,203

(22) PCT Filed: Nov. 24, 1998

(86) PCT No.: PCT/GB98/03496

§ 371 (c)(1),
(2), (4) Date: May 25, 2000

(87) PCT Pub. No.: WO99/28317

PCT Pub. Date: Jun. 10, 1999

(30) Foreign Application Priority Data

Nov. 29, 1997 (GB) .............................................. 9725244

(51) Int. Cl.$^7$ ..................... A61K 31/506; A61K 31/517; C07D 239/38; C07D 241/38
(52) U.S. Cl. ............... 514/249; 514/230.5; 514/255.05; 514/269; 514/274; 514/272; 514/341; 514/363; 514/371; 544/105; 544/331; 544/405; 544/316; 544/355; 546/271.4; 548/129; 548/204; 548/229
(58) Field of Search ........................ 514/255.05, 230.5, 514/269, 272, 341, 363, 371; 544/105, 331, 405; 546/271.4; 548/129, 204, 229

(56) References Cited

U.S. PATENT DOCUMENTS

| | | | |
|---|---|---|---|
| 4,287,351 A | 9/1981 | Bourgery et al. | 548/232 |
| 4,346,102 A | 8/1982 | Langlois et al. | 424/279 |
| 4,476,136 A | 10/1984 | Dostert et al. | 424/272 |
| 4,705,799 A | 11/1987 | Gregory | 514/376 |
| 4,942,183 A | 7/1990 | Gregory et al. | 514/376 |
| 4,948,801 A | 8/1990 | Carlson et al. | 514/307 |
| 4,977,173 A | 12/1990 | Brittelli et al. | 514/376 |
| 5,043,443 A | 8/1991 | Carlson et al. | 544/112 |
| 5,164,510 A | 11/1992 | Brickner | 548/231 |
| 5,182,403 A | 1/1993 | Brickner | 548/231 |
| 5,231,188 A | 7/1993 | Brickner | 548/221 |
| 5,523,403 A | 6/1996 | Barbachyn | 544/137 |
| 5,529,998 A | 6/1996 | Häbich et al. | 514/233.8 |
| 5,547,950 A | 8/1996 | Hutchinson et al. | 514/252 |
| 5,565,571 A | 10/1996 | Barbachyn et al. | 546/144 |
| 5,574,055 A | 11/1996 | Borgulya et al. | 514/376 |
| 5,652,238 A | 7/1997 | Brickner et al. | 514/235.8 |
| 5,654,428 A | 8/1997 | Barbachyn et al. | 544/235 |
| 5,668,286 A | 9/1997 | Yamada et al. | 546/209 |
| 5,688,792 A | 11/1997 | Barbachyn et al. | 514/235.5 |
| 5,698,574 A | 12/1997 | Reidl et al. | 514/376 |
| 5,708,169 A | 1/1998 | Hester, Jr. et al. | 549/152 |
| 5,719,154 A | 2/1998 | Tucker et al. | 514/252 |

(List continued on next page.)

FOREIGN PATENT DOCUMENTS

| | | | |
|---|---|---|---|
| AU | 24985/95 | 2/1996 | ............... C07J/1/00 |
| AU | 50735/96 | 10/1996 | ......... C07D/413/10 |
| CA | 2154024 | 1/1996 | ......... C07D/413/04 |
| EP | 0127902 | 12/1984 | ......... C07D/263/20 |
| EP | 0184170 | 6/1986 | ......... C07D/263/20 |
| EP | 0312000 | 4/1989 | ......... C07D/263/20 |

(List continued on next page.)

OTHER PUBLICATIONS

Abstracts of the 36th ICAAC (Interscience Congress of Antimicrobial Agents and Chemotherapy), New Orleans, pp. 41,52,140, (1996).

Ashtekar, D., et al., "Oxazolidinones, a New Class of Synthetic Antituberculosis Agent: In vitro and in vivo Activities of DuP–721 Against *Mycobacterium tuberculosis*", *Diagn. Microbiol. Infect. Dis.*, 14, 465–471, (1991).

Barbachyn, M., et al., "Identification of a Novel Oxazolidinone (U–100480) with Potent Antimycobacterial Activity", *J. Medical Chemistry*, 39, 680–685, (1996).

(List continued on next page.)

*Primary Examiner*—Joseph K. McKane
*Assistant Examiner*—Sonya Wright

(57) ABSTRACT

The invention concerns compounds of formula (I), (I)

wherein, for example,
   $R^1$ is of the formula —NHC(=O)$R^a$ wherein $R^a$ is (1–4C)alkyl;
   $R^2$ and $R^3$ are independently hydrogen or fluoro;
   $R^5$ and $R^6$ are, for example, hydrogen;
   $R^4$ is —X—Y—Het.;
wherein, for example,
   X is a direct bond and Y is —(CH$_2$)$_m$— or —CONH—(CH$_2$)$_m$—;
   or X is —(CH$_2$)$_n$— and Y is —S(O)$_p$—(CH$_2$)$_m$—;
   or X is —CH$_2$O— or —CH$_2$NH— and Y is —CO—(CH$_2$)$_m$—;
   wherein n is 1, 2 or 3; m is 0, 1, 2 or 3 and p is 0, 1 or 2;
   wherein Het. is a heterocyclic ring, unsaturated or saturated, optionally substituted by, for example, (1–4C)alkyl, halo, cyano, nitro or amino; pharmaceutically acceptable salts and in vivo hydrolysable ester thereof; processes for their preparation; pharmaceutical compositions containing them and their use as antibacterial agents.

16 Claims, No Drawings

U.S. PATENT DOCUMENTS

| | | | |
|---|---|---|---|
| 5,736,545 A | 4/1998 | Gadwood et al. | 514/252 |
| 5,880,118 A | 3/1999 | Barbachyn et al. | 514/211 |
| 5,922,708 A | 7/1999 | Riedl et al. | 514/236.8 |
| 5,977,149 A * | 11/1999 | Brown et al. | 514/362 |
| 5,981,528 A | 11/1999 | Gravestock | 514/252 |
| 6,096,895 A * | 8/2000 | Brown et al. | 548/110 |

FOREIGN PATENT DOCUMENTS

| | | | |
|---|---|---|---|
| EP | 0316594 | 5/1989 | C07D/263/20 |
| EP | 0352781 | 1/1990 | C07D/263/20 |
| EP | 0359418 | 3/1990 | C07D/413/04 |
| EP | 0609905 | 8/1994 | C07D/413/04 |
| EP | 0657440 | 6/1995 | C07D/263/24 |
| EP | 0693491 | 1/1996 | C07D/413/04 |
| EP | 0694543 | 1/1996 | C07D/413/04 |
| EP | 0694544 | 1/1996 | C07D/413/04 |
| EP | 0738726 | 10/1996 | C07D/417/04 |
| EP | 0789026 | 8/1997 | C07D/413/14 |
| FR | 2458547 | 1/1981 | C07D/263/16 |
| FR | 2500450 | 8/1982 | C07D/263/20 |
| GB | 2028306 | 3/1980 | C07D/263/16 |
| GB | 2053196 | 2/1981 | C07D/307/02 |
| GB | 2054575 | 2/1981 | C07D/263/20 |
| GB | 2094299 | 9/1982 | C07D/263/20 |
| GB | 2141716 | 1/1985 | C07D/263/20 |
| WO | 93/09103 | 5/1993 | C07D/263/20 |
| WO | 93/23384 | 11/1993 | C07D/263/20 |
| WO | 94/01110 | 1/1994 | A61K/31/42 |
| WO | 94/13649 | 6/1994 | C07D/263/20 |
| WO | 95/07271 | 3/1995 | C07D/263/20 |
| WO | 95/14684 | 6/1995 | C07D/263/20 |
| WO | 95/25106 | 9/1995 | C07D/413/10 |
| WO | 96/13502 | 5/1996 | C07D/413/10 |
| WO | 96/15130 | 5/1996 | C07D/491/048 |
| WO | 96/23788 | 8/1996 | C07D/413/10 |
| WO | 96/35691 | 11/1996 | C07D/487/04 |
| WO | 97/01223 | 3/1997 | C07D/263/20 |
| WO | 97/09328 | 3/1997 | C07D/413/10 |
| WO | 97/10235 | 3/1997 | C07D/307/52 |
| WO | 97/14690 | 4/1997 | C07D/307/32 |
| WO | 97/19089 | 5/1997 | C07D/498/04 |
| WO | 97/21708 | 6/1997 | C07D/413/12 |
| WO | 97/27188 | 7/1997 | C07D/413/10 |
| WO | 97/30981 | 8/1997 | C07D/263/20 |
| WO | 97/30995 | 8/1997 | C07D/413/10 |
| WO | 97/31917 | 9/1997 | C07D/413/10 |
| WO | 97/37980 | 10/1997 | C07D/263/24 |
| WO | 97/43280 | 11/1997 | C07D/405/10 |
| WO | 98/01446 | 1/1998 | C07D/413/12 |
| WO | 98/01447 | 1/1998 | C07D/413/12 |
| WO | 98/07708 | 2/1998 | C07D/261/04 |

OTHER PUBLICATIONS

Barbachyn, M., et al., "Synthesis and Antibacterial Activity of New Tropone–Substituted Phenyloxazolidinone Antibacterial Agents. 1. Identification of Leads and Importance of the Tropone Substitution Pattern.", *Bioorganic and Medicinal Chemistry Lett.*, 6, 1003–1008, (1996).

Barbachyn, M., et al., "Synthesis and Antibacterial Activity of New Tropone–Substituted Phenyloxazolidinone Antibacterial Agents. 2. Modification of the Phenyl Ring—the Potentiating Effect of Fluorine Substitution on In Vivo Activity.", *Bioorganic and Medicinal Chemistry Lett.*, 6, 1009–1014, (1996).

Barry, A., et al., "In Vitro Evaluation of DuP 105 and DuP 721, Two New Oxazolidinone Antimicrobial Agents", *Antimicrobial Agents and Chemotherapy*, 32, 150–152, (1988).

Borthwick, A., et al., "5–(Acetamidomethyl)–3–Aryldihydrofuran–2–ones, and 5–(Acetamidomethyl)–3–Aryltetrahydrofuran–2–ones, Two New Classes of Antibacterial Agents", *Med. Chem. Res.*, 6, 22–27, (1996).

Brickner, S., et al., "Oxazolidinone Antibacterial Agents", *Current Pharmaceutical Design*, 2, 175–194, (1996).

Brickner, S., et al., "Synthesis and Antibacterial Activity of U–100592 and U–100766, Two Oxazolidinone Antibacterial Agents for the Potential Treatment of Multidrug–Resistant Gram–Positive Bacterial Infections", *J. Medical Chemistry*, 39, 673–679, (1996).

Brumfitt, W., et al., "Antibacterial Oxazolidinones: In Vitro Activity of a New Analogue, E3709", *Diagn. Microbiol. Infect. Dis.*, 15, 621–625, (1992).

Brumfitt, W., et al., "In–vitro Microbiological Activities of DuP 105 and DuP 721, Novel Synthetic Oxazolidinones", *J. Antimicrobial Chemotherapy*, 21, 711–720, (1988).

Brumfitt, W., et al., "Variation in Response of Gram–Positive cocci to the Combination DuP 721 and ciprofloxacin", *J. Antimicrob. Chemotherapy*, 24, 465–466, (1989).

Daly, J., et al., "Activity and Mechanism of Action of DuP 105 and DuP 721, New Oxazolidinone Compounds", *J. Antimicrobial Chemotherapy*, 21, 721–730, (1988).

Denis, A., et al., "5–Aryl–beta,gamma Butenolide, A New Class of Antibacterial Derived from the N–Aryl Oxazolidinone DUP 721", *Bioorganic and Medicinal Chemistry Lett.*, 4, 1925–1930, (1994).

Dostert, P., et al., "Structural Modifications in Oxazolidinone Series Leading to Type A or B Selective Monoamine Oxidase Inhibitors", *Int. Congress Series; Excerpta Medica*, 564, 197–208, (1982).

Eliopoulos, G., et al., "In Vitro Activities of New Oxazolidinone Antimicrobial Agents against Enterococci", *Antimicrobial Agents and Chemotherapy*, 40, 1745–1747, (1996).

Eustice, D., et al., "An Automated Pulse Labelling Method for Structure–Activity Relationship Studies with Antibacterial Oxazolidinones", *Drugs Exp. Clin. Res.*, 16, 149–155, (1990).

Eustice, D., et al., "Mechanism of Action of DuP 721: Inhibition of an Early Event during Initiation of Protein Synthesis", *Antimicrobial Agents and Chemotherapy*, 32, 1218–1222, (1988).

Eustice, D., et al., "The Mechanism of Action of DuP 721, a New Antibacterial Agent: Effects on Macromolecular Synthesis", *Biochem. and Biophys. Res. Comm.*, 150, 965–971, (1988).

Lund, J., et al., "Hypersegmented Megakaryocytes and Megakaryocytes with Multiple Separate Nuclei in Dogs Treated with PNU–100592, an Oxazolidinone Antibiotic", *Toxicologic Pathology*, 25, 339–343, (1997).

Maple, P., et al., "Comparative in–vitro activity of vancomycin, teicoplanin, ramoplanin (formerly A16686), paldimycin, DuP 721 and DuP 105 against methicillin and gentamicin resistant *Staphylococcus aureus*", *J. Antimicrobial Chemotherapy*, 23, 517–525, (1989).

Mason, E., et al., "In Vitro Activities of Oxazolidinones U–100592 and U–100766 against Penicillin–Resistant and Cephalosporin–Resistant Strains of *Streptococcus pneumoniae*", *Antimicrobial Agents and Chemotherapy*, 40, 1039–1040, (1996).

Mini, E., et al., "Comparative in Vitro Activity of the New Oxazolidinones DuP 721 and DuP 105 against Staphylococci and Streptococci", *Eur. J. Clin. Microbiol. Infect. Dis.*, 8 (3), pp. 256–260, (1989).

Mulazimoglu, L., et al., "In Vitro Activities of Two Novel Oxazolidinones (U100592 and U100766, a New Fluoroquinolone (Trovafloxacin), and Dalfopristin–Quinupristin against *Staphylococcus aureus* and *Staphylococcus epidermis*", *Antimicrobial Agents and Chemotherapy*, 40, 2428–2430, (1996).

Neu, H., et al., "In Vitro Activities of Two Oxazolidinone Antimicrobial Agents, DuP 721 and DuP 105", *Antimicrobial Agents and Chemotherapy*, 32, 580–583, (1988).

Park, C., et al., "Antibacterials. Synthesis and Structure–Activity Studies of 3–Aryl–2–oxooxazolidines. 4. Multiply–Substituted Aryl Derivatives", *J. Med. Chem.*, 53, 1156–1165, (1992).

Ranaldi, G., et al., "Transport of the Antibacterial Agent Oxazolidin–2–One and Derivatives across Intestinal (Caco–2) and Renal (MDCK) Epithelial Cell Lines", *Antimicrobial Agents and Chemotherapy*, 40, 652–658, (1996).

Schaadt, R., et al., "Serum Inhibitory Titers and Serum Bactericidal Titers for Human Subjects Receiving Multiple Doses of the Antibacterial Oxazolidinones Eperezolid and Linezolid", *Diagn. Microbiol. Infect. Dis.*, 28, 201–204, (1997).

Schaus, S., et al., "Dynamic Kinetic Resolution of Epichlorohydrin via Enantioselective Catalytic Ring Operation with TMSN3. Practical Synthesis of Aryl Oxazolidinone Antibacterial Agents", *Tetrahedron Lett.*, 37, 7937–7940, (1996).

Scholl, J., et al., "Micellar Electrokinetic Chromatography as a Generalized Alternative to High–Performance Liquid Chromatography for Purity Determination of a Class of Investigational Antibacterial Drugs", *J. of Chromatography B*, 695, 147–156, (1997).

Seneci, P., et al., "Synthesis and Antimicrobial Activity of Oxazolidin–2–ones and Related Heterocycles", *J. Chem. Soc. Perkin Trans.* 1, 16, 2345–2351, (1994).

Shinabarger, D., et al., "Mechanism of Action of Oxazolidinones: Effects of Linezolid and Eperezolid on Translation Reactions", *Antimicrobial Agents and Chemotherapy*, 41, 2132–2136, (1997).

Silverman, R., et al., "The Oxazolidinone Antibacterial Agent DuP 105 Does Not Act On Cell Wall Biosynthesis Or On A Beta–Lactamase", *Biochemical and Biophysical Research Comm.*, 195, 1077–1080, (1993).

Slee, A., et al., "Oxazolidinones, a New Class of Synthetic Antibacterial Agents: In Vitro and In Vivo Activities of DuP 105 and DuP 721", *Antimicrobial Agents and Chemothrapy*, 31, 1791–1797, (1987).

Spangler, S., et al., "Activities of RPR 106972 (a New Oral Streptogramin), Cefditoren (A New Oral Cephalosporin), Two New Oxazolidinones (U–100592 and U–100766), and Other Oral and Parenteral Agents against 203 Penicillin–Susceptible and –Resistant Pneumococci", *Antimicrobial Agents and Chemotherapy*, 40, 481–484, (1996).

Takagi, H., et al., "Safety Pharmacology Evaluation of the Oxazolidinone, U–100766", *Society of Toxicologists Annual Meeting*, Abstract No. 564, p. 110, (1996).

Tucker, J.A., et al., "Piperazinyl Oxazolidinone Antibacterial Agents Containing a Pyridine, Diazene, or Triazene Heteroaromatic Ring", *J. Med. Chem.* 41, pp. 3727–2735, (1998).

Wang, C., et al., "Chiral Synthesis of DUP 721, A New Antibacterial Agent", *Tetrahedron*, 45 (5), pp. 1323–1326, (1989).

Worth, S., et al., "Quality Control Guidelines for Amoxicillin, Amoxicillin–Clavulanate, Azithromycin, Piperacillin–Tazobactam, Roxithromycin, Ticarcillin, Ticarcillin–Clavulanate, Trovafloxacin (CP 99,219), U–100592, and U–100766 for Various National Committee . . . ", *Diagn. Microbiol. Infect. Dis.*, 24, 87–91, (1996).

Zurenko, G., et al., "In Vitro Activities of U–100592 and U–100766, Novel Oxazolidinone Antibacterial Agents", *Antimicrobial Agents and Chemotherapy*, 40, 839–845, (1996).

Zurenko, G., et al., "Oxazolidinone antibacterial agents: development of the clinical candidates eperezolid and linezolid", *Exp. Opin. Invest. Drugs*, 6, 151–158, (1997).

Ford, C., et al., "In Vivo Activities of U–100592 and U–100766, Novel Oxazolidinone Antimicrobial Agents, against Experimental Bacterial Infections", *Antimicrobial Agents and Chemotherapy*, 40, 1508–1513, (1996).

Grega, K., et al., "Regioselective Metalation of Fluoroanilines. An Application to the Synthesis of Fluorinated Oxazolidinone Antibacterial Agents, against Experimental Bacterial Infections", *Antimicrobial Agentds and Chemotherapy*, 40, 1508–1513, (1996).

Gregory, W., et al., "Antibacterials. Synthesis and Structure–Activity Studies of 3–Aryl–2–oxooxazolidines. 1. The "B" Group", *J. Med. Chem.*, 32, 1673–1681, (1989).

Gregory, W., et al., "Antibacterial. Synthesis and Structure–Activity Studies of 3–Aryl–2–oxooxazolidines. 2. The "A" Group", *J. Med. Chem.*, 33, 2569–2578, (1990).

Hutchinson, D., et al., "Piperazinyl Oxazolidinones: Structure Activity Relationshipd of a New Class of Oxazolidinone Antibacterial Agents", *Abstract: Interscience Congress of Antimicrobial Agents and Chemotherapy*, 8–14, (Sep. 17–20, 1995).

Jones, R., et al., "In Vitro Antimicrobial Activities and Spectra of U–100592 and U–100766, Two Novel Fluorinated Oxazolidinones", *Antimicrobial Agents and Chemotherapy*, 40, 720–726, (1996).

Jorgensen, J., et al., "In Vitro Activities of the Oxazolidinone Antibiotics U–100592 and U–100766 against Staphylococcus aureus and Coagulase–Negative Staphylococcus Species", *Antimicrobial Agents and Chemotherapy*, 41, 465–467, (Feb. 1997).

Kaatz, G., et al., "In Vitro Activities of Oxazolidinone Compounds U100592 and U100766 against Staphylococcus aureus and Staphylococcus epidermis", *Antimicrobial Agents and Chemotherapy*, 40, 799–801, (1996).

Lin, A., et al., "The Oxazolidinone Eperezolid Binds to the 50S Ribosomal Subunit and Competes with Bindin of Chloramphenicol and Lincomycin", *Antimicrobial Agents and Chemotherapy*, 41, 2127–2131, (1997).

Lizondo, J., et al., "Linezolid U–100766", *Drugs of the Future, 21*, 1116–1123, (1996).

\* cited by examiner

SUBSTITUTED PHENYLOXAZOLIDINONES AND THEIR USE AS ANTIBIOTICS

This is a U.S. National Stage filing under 35 U.S.C. 371 of International Patent Application No. PCT/GB98/03496, filed Nov. 24, 1998, which is based on British Patent Application No. 9725244.9, filed Nov. 29, 1997.

The present invention relates to antibiotic compounds and in particular to antibiotic compounds containing an oxazolidinone ring. This invention further relates to processes for their preparation, to intermediates useful in their preparation, to their use as therapeutic agents and to pharmaceutical compositions containing them.

The international microbiological community continues to express serious concern that the evolution of antibiotic resistance could result in strains against which currently available antibacterial agents will be ineffective. In general, bacterial pathogens may be classified as either Gram-positive or Gram-negative pathogens. Antibiotic compounds with effective activity against both Gram-positive and Gram-negative pathogens are generally regarded as having a broad spectrum of activity. The compounds of the present invention are regarded primarily as effective against Gram-positive pathogens because of their particularly good activity against such pathogens.

Gram-positive pathogens, for example Staphylococci, Enterococci, Streptococci and mycobacteria, are particularly important because of the development of resistant strains which are both difficult to treat and difficult to eradicate from the hospital environment once established. Examples of such strains are methicillin resistant staphylococcus (MRSA), methicillin resistant coaguiase negative staphylococci (MRCNS), penicillin resistant *Streptococcus pneumoniae* and multiply resistant *Enterococcus faecium*.

The major clinically effective antibiotic for treatment of such resistant Gram-positive pathogens is vancomycin. Vancomycin is a glycopeptide and is associated with nephrotoxicity and ototoxicity. Furthermore, and most importantly, antibacterial resistance to vancomycin and other glycopeptides is also appearing. This resistance is increasing at a steady rate rendering these agents less and less effective in the treatment of Gram-positive pathogens.

The present inventors have discovered a class of antibiotic compounds containing an oxazolidinone ring which has useful activity against Gram-positive pathogens including MRSA and MRCNS and, in particular, against various strains exhibiting resistance to vancomycin and against *E. faecium* strains resistant to both aminoglycosides and clinically used β-lactams.

We have now discovered a range of compounds which have good activity against a broad range of Gram-positive pathogens including organisms known to be resistant to most commonly used antibiotics. In comparison with compounds described in the art (Walter A. Gregory et al in J.Med.Chem. 1990, 33, 2569–2578 and Chung-Ho Park et al in J.Med.Chem. 1992, 35, 1156–1165) the compounds also possess a favourable toxicological profile.

Accordingly the present invention provides a compound of the formula (I):

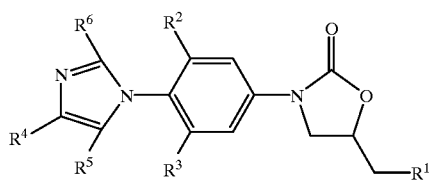

(I)

wherein $R^1$ is hydroxy, amino, chloro, fluoro, (1–4C) alkanesulfonyloxy, azido, (1–4C)alkoxy, or of the formula —NHC(=O)$R^a$ wherein $R^a$ is hydrogen, (1–4C) alkoxy, chloromethyl, dichloromethyl, cyanomethyl, methoxymethyl, acetylmethyl or (1–4C)alkyl;

$R^2$ and $R^3$ are independently hydrogen or fluoro;

$R^5$ and $R^6$ are independently selected from hydrogen, (1–4C)alkyl, halo and trifluoromethyl;

$R^4$ is —X—Y—Het.;

wherein X is a direct bond or —CH(OH)— and Y is —(CH$_2$)$_m$—, —(CH$_2$)$_n$—NH—(CH$_2$)$_m$—, —CO—(CH$_2$)$_m$—, —CONH—(CH$_2$)$_m$—, —C(=S)NH—(CH$_2$)$_m$— or —C(=O)O—(CH$_2$)$_m$—;

or wherein X is —(CH$_2$)$_n$— or —CH(Me)—(CH$_2$)$_m$— and Y is —(CH$_2$)$_m$—NH—(CH$_2$)$_m$—, —CO—(CH$_2$)$_m$—, —CONH—(CH$_2$)$_m$—, C(=S)NH—(CH$_2$)$_m$—, —C(=O)O—(CH$_2$)$_m$— or —S(O)$_p$—(CH$_2$)$_m$—;

or wherein X is —CH$_2$O—, —CH$_2$NH— or —CH$_2$N(R)— [wherein R is (1–4C)alkyl] and Y is —CO—(CH$_2$)$_m$—, —CONH—(CH$_2$)$_m$— or —C(=S)NH—(CH$_2$)$_m$—; and additionally Y is —SO$_2$— when X is —CH$_2$NH— or —CH$_2$N(R)— [wherein R (1–4C) alkyl], and Y is —(CH$_2$)$_m$— when X is —CH$_2$O— or —CH$_2$N(R)—;

wherein n is 1, 2 or 3; m is 0, 1, 2 or 3 and p is 0, 1 or 2; and when Y is —(CH$_2$)$_m$—NH—(CH$_2$)$_m$— each m is independently selected from 0, 1, 2 or 3;

wherein Het. is a heterocyclic ring [which heterocyclic ring may be unsaturated (linked via either a ring carbon or ring nitrogen atom to —X—Y—) or saturated (linked via a ring nitrogen atom to —X—Y—), with the proviso that when it is unsaturated and linked via nitrogen to —X—Y— the ring is not quaternised] which heterocyclic ring is optionally substituted on an available carbon atom by up to three substituents independently selected from (1–4C)alkyl [optionally substituted by trifluoromethyl, (1–4C)alkyl S(O)$_p$— (wherein p is 0, 1 or 2), carbamoyl, N-(1–4C) alkyicarbamoyl, di(N-(1–4C)alkyl)carbamoyl, (1–4C) alkoxy, (1–4C)alkoxycarbonyl, cyano, nitro, amino, N-(1–4C)alkylamino, di(N-(1–4C)alkyl)amino or (1–4C)alkanoylamino], halo, trifluoromethyl, (1–4C) alkyl S(O)$_p$(wherein p is 0, 1 or 2), carboxy, (1–4C) alkoxycarbonyl, carbamoyl, N-(1–4C)alkylcarbamoyl, di(N-(1–4C)alkyl)carbamoyl, (2–4C)alkenyl, cyano, nitro, amino, (2–4C)alkanoylamino, (1–4C)alkoxy, di(N-(1–4C)alkyl)aminomethylimino, hydroxy, oxo or thioxo (=S); and optionally substituted on an available nitrogen atom (if the ring will not thereby be quaternised) by (1–4C)alkyl [optionally substituted by trifluoromethyl, (1–4C)alkyl S(O)$_p$— (wherein p is 0, 1 or 2), (1–4C)alkoxy, (1–4C)alkoxycarbonyl, carbamoyl, N-(1–4C)alkylcarbamoyl, di(N-(1–4C) alkyl)carbamoyl, cyano, nitro, amino, N-(1–4C) alkylamino, di(N-(1–4C)alkyl)amino or (1–4C) alkanoylamino] or oxo (to form an N-oxide); and pharmaceutically acceptable salts thereof.

In a further aspect of the invention there is provided a compound of the formula (I) as described hereinabove, wherein when X is a direct bond, Y is additionally —CON(R)— (CH$_2$)$_m$— [wherein R is (1–4C)alkyl], and the optional substituents on an available carbon atom in the Het. heterocyclic ring additionally include amino.

The term 'alkyl' includes straight chained and branched structures. For example, (1–4C)alkyl includes propyl, iso-propyl and t-butyl.

Examples of (1–4C)alkyl include methyl, ethyl, propyl, isopropyl and t-butyl; examples of N-(1–4C)alkylcarbamoyl include methylcarbamoyl and ethylcarbamoyl; examples of di(N-(1–4C)alkyl)carbamoyl include di(methyl)carbamoyl and di(ethyl)carbamoyl; examples of (1–4C)alkylS(O)$_p$— include methylthio, ethylthio, methylsulfinyl, ethylsulfinyl, methylsulfonyl and ethylsulfonyl; examples of (2–4C) alkenyl include allyl and vinyl; examples of (1–4C)alkoxy include methoxy, ethoxy and propoxy; examples of (2–4C) alkanoylamino include acetamido and propionylamino; examples of N-(1–4C)alkylamino include methylamino and ethylamino; example of di-(N-(1–4C)alkyl)amino include di-N-methylamino, di-(N-ethyl)amino and N-ethyl-N-methylamino; examples of (1–4C)alkoxycarbonyl include methoxycarbonyl and ethoxycarbonyl; examples of halo include fluoro, chloro and bromo; examples of di-(N-(1–4C) alkyl)aminomethylimino include dimethylaminomethylimino and diethylaminomethylimino and examples of (1–4C)alkanesulfonyloxy include methylsulfonyloxy and ethylsulfonyloxy.

A heterocyclic ring means a 5- or 6-membered monocyclic ring or a 5/6 or 6/6 bicyclic ring (linked via either, or any, of the rings) containing up to four heteroatoms selected independently from O, S and N. An unsaturated ring means a fully unsaturated (aromatic) ring and partially unsaturated ring systems (such as, for example, tetrahydropyridine). Preferred examples of unsaturated 5- or 6-membered heterocyclic groups with up to four heteroatoms selected independently from O, S and N are furan, pyrrole, thiophene, those containing one, two or three N atoms (for example, pyrazole, imidazole, pyridine, pyrimidine, pyrazine, pyridazine, 1,2,3- and 1,2,4-triazole), two N atoms and one S atom (for example 1,2,4- and 1,3,4-thiadiazole, ), one N and one O atom (for example oxazole, isoxazole and oxazine) and one N and one S atom (for example thiazole and isothiazole). Unsaturated 5-membered heterocyclic groups are preferred. Thiazole is particularly preferred. Links via a ring carbon atom are preferred.

Preferred examples of a 5/6 or 6/6 bicyclic ring (linked via either of the rings) containing up to four heteroatoms selected independently from O, S and N are, for example, indole, quinoline, isoquinoline, benzpyrrole, benzpyrazole, benzimidazole, quinoxaline, benzthiazole, benzoxazole, benzthiadiazole, benztriazole and 1,4-benzodioxan. Preferred are 5/6 bicyclic rings, particularly those containing up to two heteroatoms only, such as benzthiazole and benzoxazole, especially benzthiazole. Links via a ring carbon atom are preferred.

It is to be understood that when a value for —X— is a two-atom link and is written, for example., as —CONH— it is the left hand part (—CO— here) which is bonded to the imidazole ring in formula (I) and the right hand part (—NH— here) which is bonded to —Y— in the definition of R$^4$. Similarly, when —Y— is a two-atom link and is written, for example, as —CONH— it is the left hand part of —Y—(—CO— here) which is bonded to the right hand part of —X—, and the right hand part of —Y—(—NH— here) which is bonded to the Het. moiety in the definition of R$^4$.

Suitable pharmaceutically-acceptable salts include acid addition salts such as methanesulfonate, fumarate, hydrochloride, hydrobromide, citrate, maleate and salts formed with phosphoric and sulfuric acid. In another aspect suitable salts are base salts such as an alkali metal salt for example sodium, an alkaline earth metal salt for example calcium or magnesium, an organic amine salt for example triethylamine, morpholine, N-methylpiperidine, N-ethylpiperidine, procaine, dibenzylamine, N,N-dibenzylethyiamine or amino acids for example lysine.

There may be more than one cation or anion depending on the number of charged functions and the valency of the cations or anions. A preferred pharmaceutically-acceptable salt is the sodium salt.

However, to facilitate isolation of the salt during preparation, salts which are less soluble in the chosen solvent may be preferred whether pharmaceutically-acceptable or not.

The compounds of the formula (I) may be administered in the form of a pro-drug which is broken down in the human or animal body to give a compound of the formula (I). Examples of pro-drugs include in-vivo hydrolysable (in-vivo cleavable) esters of a compound of the formula (I).

An in-vivo hydrolysable ester of a compound of the formula (I) containing carboxy or hydroxy group is, for example, a pharmaceutically-acceptable ester which is hydrolysed in the human or animal body to produce the parent acid or alcohol. Suitable pharmaceutically-acceptable esters for carboxy include (1–6C)alkoxymethyl esters for example methoxymethyl, (1–6C)alkanoyloxymethyl esters for example pivaloyloxymethyl, phthalidyl esters, (3–8C) cycloalkoxycarbonyloxy(1–6C)alkyl esters for example 1-cyclohexylcarbonyloxyethyl; 1,3-dioxolen-2-onylmethyl esters for example 5-methyl-1,3-dioxolen-2-onylmethyl; and (1–6C)alkoxycarbonyloxyethyl esters for example 1-methoxycarbonyloxyethyl and may be formed at any carboxy group in the compounds of this invention.

An in-vivo hydrolysable ester of a compound of the formula (I) containing a hydroxy group includes inorganic esters such as phosphate esters and α-acyloxyalkyl ethers and related compounds which as a result of the in-vivo hydrolysis of the ester breakdown to give the parent hydroxy group. Examples of α-acyloxyalkyl ethers include acetoxymethoxy and 2,2-dimethylpropionyloxymethoxy. A selection of in-vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

The compounds of the present invention have a chiral centre at the C-5 position. The pharmaceutically active enantiomer is of the formula (IA):

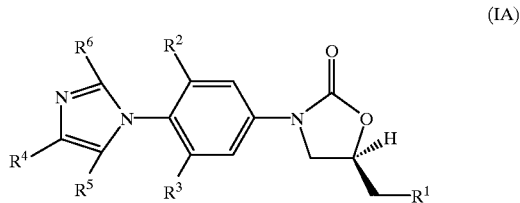

(IA)

The present invention includes the pure enantiomer depicted above or mixtures of the 5(R) and 5(S) enantiomers, for example a racemic mixture. If a mixture of 5(R) and 5(S) is used, a larger amount (depending up on the ratio of the enantiomers) will be required to achieve the same effect as the same weight of the pharmaceutically active enantiomer. Furthermore, some compounds of the formula (I) may have other chiral centres, for example when X is —CH(Me)—.

It will be appreciated that when the Het. moiety in R$^4$ is optionally substituted by hydroxy, oxo or thioxo the phenomenon of tautomerism may be present depending upon the nature of the Het. moiety. Thus, for example, in fully unsaturated (aromatic) systems a hydroxy substituent may represent one tautomeric form, and an oxo substituent the other tautomeric form. The invention includes all tautomeric forms which possess antibacterial activity.

Preferably $R^1$ is of the formula —NHC(=O)$R^a$ wherein $R^a$ is hydrogen, methoxy, amino, chloromethyl, dichloromethyl, cyanomethyl, methoxymethyl, acetylmethyl or (1–4C)alkyl.

Yet more preferably $R^1$ is of the formula —NHC(=O)(1–4C)alkyl.

Most preferably $R^1$ is acetamido.

Preferably one of $R^2$ and $R^3$ is hydrogen and the other is fluoro.

Preferably $R^5$ and $R^6$ are hydrogen.

Preferably the Het. moiety in $R^4$ is unsaturated, ie. fully unsaturated (aromatic) ring or partially unsaturated ring systems. Preferably the Het. moiety in $R^4$ ring is linked via a ring carbon atom.

Preferred values for the Het. moiety in $R^4$ are furan, thiophene, pyrazole, imidazole, pyridine, pyrimidine, pyrazine, pyridazine, 1,2,3- and 1,2,4-triazole, 1,2,4- and 1,3,4-thiadiazole, oxazole, isoxazole, thiazole, isothiazole, indole, quinoline, isoquinoline, benzpyrazole, benzimidazole, quinoxaline, benzthiazole, benzoxazole, benzthiadiazole, benztriazole and 1,4-benzodioxan.

Preferred values for —X—Y— links are —CH$_2$S—, —CH$_2$O—CO—, —CH$_2$NH—, —CH$_2$NHCO— and —CONH—.

Other preferred values for —X—Y— links are a direct link, —CH$_2$SO$_2$—, —CH$_2$—, —CH$_2$NHSO$_2$—, —CH$_2$O—CO—CH$_2$—, —CO—O—CH$_2$—, —CO—O—CH$_2$—CH$_2$—, —CONH—CH$_2$—, —CONH—CH$_2$—CH$_2$—, —CO— and —CON(Me)—.

Preferred optional substituents (preferably, zero, one or two) on an available carbon atom of the Het. moiety of $R^4$ are (1–4C)alkyl, halo, cyano, nitro. amino, (2–4C)alkanoylamino, (1–4C)alkoxy, hydroxy, oxo and thioxo (=S).

Preferred optional substituents (preferably, zero or one) on an available nitrogen atom of the Het. moiety of $R^4$ are (1–4C)alkyl, especially methyl, and oxo (to form an N-oxide).

Accordingly, in a particular aspect of the present invention there is provided a compound of the formula (I) in which $R^1$ is acetamido; one of $R^2$ and $R^3$ is hydrogen and the other is fluoro; $R^5$ and $R^6$ are hydrogen; the —X—Y— link is —CH$_2$S—, —CH$_2$O—CO—, —CH$_2$NH—, —CH$_2$NHCO— or —CONH—; the Het. moiety in $R^4$ is a fully unsaturated (aromatic) ring linked via a ring carbon atom and selected from furan, thiophene, pyrazole, imidazole, pyridine, pyrimidine, pyrazine, pyridazine, 1,2,3- and 1,2,4-triazole, 1,2,4- and 1,3,4-thiadiazole, oxazole, isoxazole, thiazole, isothiazole, indole, quinoline, isoquinoline, benzpyrazole, benzimidazole, quinoxaline, benzthiazole, benzoxazole, benzthiadiazole, benztriazole and 1,4-benzodioxan; wherein the Het moiety is optionally substituted by up to two substituents on an available carbon atom selected from (1–4C)alkyl, halo, cyano, nitro, amino, (2–4C)alkanoylamino, (1–4C)alkoxy, hydroxy, oxo and thioxo (=S), and optionally substituted by a substituent on an available nitrogen atom selected from (1–4C)alkyl and oxo; and pharmaceutically-acceptable salts thereof.

Of the compounds in the above particular aspect, those in which the Het. moiety is a monocyclic ring are preferred.

An especially preferred compound of the invention is selected from the group consisting of:

N-[(5S)-3-(3-Fluoro-4-(4-pyrimidin-2-ylthiomethylimidazol-1-yl)phenyl)-2-oxooxazolidin-5-ylmethyl]acetamide;

N-[(5S)-3-(3-Fluoro-4-(4-(2-furoyloxymethyl)imidazol-1-yl)phenyl)-2-oxooxazolidin-5-yl-methyl]acetamide;

N-[(5S)-3-(3-Fluoro-4-(4-(5-nitropyridin-2-ylaminomethyl)imidazol-1-yl)phenyl)-2-oxooxazolidin-5-ylmethyl]acetamide;

N-[(5S)-3-(3-Fluoro-4-(4-(quinoxalin-2-ylcarbonylaminomethyl)imidazol-1-yl)phenyl)-2-oxooxazolidin-5-ylmethyl]acetamide;

N-[(5S)-3-(3-Fluoro-4-(4-(thiazol-2-ylaminocarbonyl)imidazol-1-yl)phenyl)-2-oxooxazolidin-5-ylmethyl]acetamide; and pharmnaceutically-acceptable salts thereof.

Of the above, N-[(5S)-3-(3-Fluoro-4-(4-(thiazol-2-ylaminocarbonyl)imidazol-1-yl)phenyl)-2-oxooxazolidin-5-ylmethyl]acetamide is especially preferred.

A further especially preferred compound of the invention is N-[(5S)-3-(3-Fluoro-4-(thiazol-2-ylimidazol-1-yl)phenyl)-2-oxooxazolidin-5-yl-methyl]acetamide; and pharmaceutically-acceptable salts thereof.

In a further aspect the present invention provides a process for preparing a compound of the formula (I) or a pharmaceutically acceptable salt thereof. The compounds of the formula (I) may be prepared by deprotecting a compound of the formula (II):

(II)

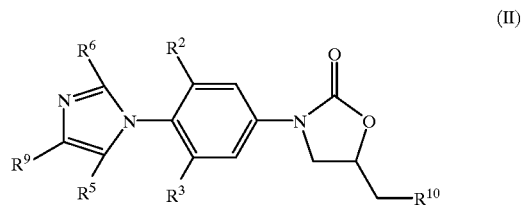

wherein $R^2$, $R^3$, $R^5$ and $R^6$ are as hereinabove defined, $R^9$ is $R^4$ or protected $R^4$ and $R^{10}$ is $R^1$ or protected $R^1$, and thereafter if necessary forming a pharmaceutically acceptable salt.

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower" signifies that the group to which it is applied preferably has 1–4 carbon atoms. It will be understood that these examples are not exhaustive. Where specific examples of methods for the removal of protecting groups are given below these are similarly not exhaustive. The use of protecting groups and methods of deprotection not specifically mentioned is of course within the scope of the invention.

A carboxy protecting group may be the residue of an ester-forming aliphatic or araliphatic alcohol or of an ester-forming silanol (the said alcohol or silanol preferably containing 1–20 carbon atoms).

Examples of carboxy protecting groups include straight or branched chain (1–12C)alkyl groups (eg isopropyl, t-butyl); lower alkoxy lower alkyl groups (eg methoxymethyl, ethoxymethyl, isobutoxymethyl; lower aliphatic acyloxy lower alkyl groups, (eg acetoxymethyl, propionyloxymethyl, butyryloxymethyl, pivaloyloxymethyl); lower alkoxycarbonyloxy lower alkyl groups (eg 1-methoxycarbonyloxyethyl, 1-ethoxycarbonyloxyethyl); aryl lower alkyl groups (eg p-methoxybenzyl, o-nitrobenzyl, p-nitrobenzyl, benzhydryl and phthalidyl); tri(lower alkyl)silyl groups (eg trimethylsilyl and t-butyldimethylsilyl); tri(lower alkyl)silyl lower alkyl groups (eg trimethylsilylethyl); and (2–6C)alkenyl groups (eg allyl and vinylethyl).

Methods particularly appropriate for the removal of carboxyl protecting groups include for example acid-, metal- or enzymically-catalysed hydrolysis.

Examples of hydroxy protecting groups include lower alkenyl groups (eg allyl); lower alkanoyl groups (eg acetyl); lower alkoxycarbonyl groups (eg t-butoxycarbonyl); lower alkenyloxycarbonyl groups (eg allyloxycarbonyl); aryl lower alkoxycarbonyl groups (eg benzoyloxycarbonyl, pmethoxybenzyloxycarbonyl, o-nitrobenzyloxycarbonyl, pnitrobenzyloxycarbonyl); tri lower alkyl/arylsilyl groups (eg trimethylsilyl, t-butyldimethylsilyl, t-butyldiphenylsilyl); aryl lower alkyl groups (eg benzyl) groups; and triaryl lower alkyl groups (eg triphenylmethyl).

Examples of amino protecting groups include formyl, aralkyl groups (eg benzyl and substituted benzyl, eg p-methoxybenzyl, nitrobenzyl and 2,4-dimethoxybenzyl, and triphenylmethyl); di-p-anisylmethyl and furylmethyl groups; lower alkoxycarbonyl (eg t-butoxycarbonyl); lower alkenyloxycarbonyl (eg allyloxycarbonyl); aryl lower alkoxycarbonyl groups (eg benzyloxycarbonyl, p-methoxybenzyloxycarbonyl, o-nitrobenzyloxycarbonyl, p-nitrobenzyloxycarbonyl; trialkylsilyl (eg trimethylsilyl and t-butyldimethylsilyl); alkylidene (eg methylidene); benzylidene and substituted benzylidene groups.

Methods appropriate for removal of hydroxy and amino protecting groups include, for example, acid-, metal- or enzymically-catalysed hydrolysis, for groups such as o-nitrobenzyloxycarbonyl, photolytically and for groups such as silyl groups, fluoride.

Examples of protecting groups for amide groups include aralkoxymethyl (eg. benzyloxymethyl and substituted benzyloxymethyl); alkoxymethyl (eg. methoxymethyl and trimethylsilylethoxymethyl); tri alkyl/arylsilyl (eg. trimethylsilyl, t-butyldimethylsily, t-butyldiphenylsilyl); tri alkyl/arylsilyloxymethyl (eg. t-butyldimethylsilyloxymethyl, t-butyldiphenylsilyloxymethyl); 4-alkoxyphenyl (eg. 4-methoxyphenyl); 2,4-di(alkoxy)phenyl (eg. 2,4-dimethoxyphenyl); 4-alkoxybenzyl (eg. 4-methoxybenzyl); 2,4-di(alkoxy)benzyl (eg. 2,4-di(methoxy)benzyl); and alk-1-enyl (eg. allyl, but-1-enyl and substituted vinyl eg. 2-phenylvinyl).

Aralkoxymethyl, groups may be introduced onto the amide group by reacting the latter group with the appropriate aralkoxymethyl chloride, and removed by catalytic hydrogenation. Alkoxymethyl, tri alkyl/arylsilyl and tri alkyl/silyl groups may be introduced by reacting the amide with the appropriate chloride and removing with acid, or in the case of the silyl containing groups fluoride ions. The alkoxyphenyl and alkoxybenzyl groups are conveniently introduced by arylation or alkylation with an appropriate halide and removed by oxidation with ceric ammonium nitrate. Finally alk-1-enyl groups may be introduced by reacting the amide with the appropriate aldehyde and removed with acid.

For further examples of protecting groups see one of the many general texts on the subject, for example, 'Protective Groups in Organic Synthesis' by Theodora Green (publisher: John Wiley & Sons).

In another aspect of the present invention the compounds of the formulae (I) and (II) and pharmaceutically acceptable salts thereof can be prepared:

(a) by modifying a substituent in or introducing a substituent into another compound of the formula (I) or (II), or modifying a linking group in another compound of the formula (I) or (II);

(b) by reaction of a compound of the formula (III) with a compound of the formula Het—Y—L$^1$ [wherein L$^1$ and L$^2$ are independently hydrogen or a leaving group], or with a compound capable of forming a Het. moiety [wherein L$^2$ may form part of the final Het. moiety], or with a Het—Y—L$^1$ compound such that —Y—L$^1$ or L$^2$—X— (or a part thereof) may form part of the final —X—Y— link:

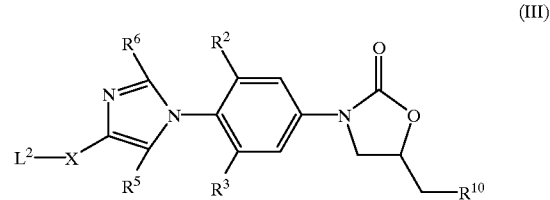

(III)

(c) when R$^1$ or R$^{10}$ is of the formula —NHC(=O)R$^a$, by introducing —C(=O)R$^a$ into a compound of the formula (I) or (II) wherein R$^1$ or R$^{10}$ is amino;

(d) when R$^1$ or R$^{10}$ is amino, by reducing a compound of the formula (I) or (II) wherein R$^1$ or R$^{10}$ is azido;

(e) when R$^1$ or R$^{10}$ is azido, by reacting a compound of the formula (IV) [wherein R$^{12}$ is mesyloxy, tosyloxy or a phosphate ester] with a source of azide:

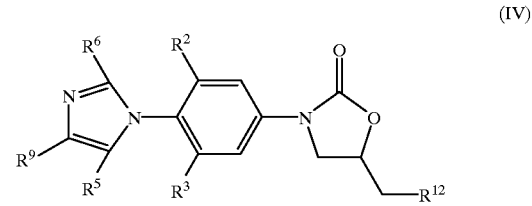

(IV)

(f) when R$^1$ or R$^{10}$ is hydroxy, by reacting a compound of the formula (V) with a compound of the formula (VI) [wherein R$^{13}$ is (1–6C)alkyl or benzyl, and R$^{14}$ is (1–5 6C)alkyl]:

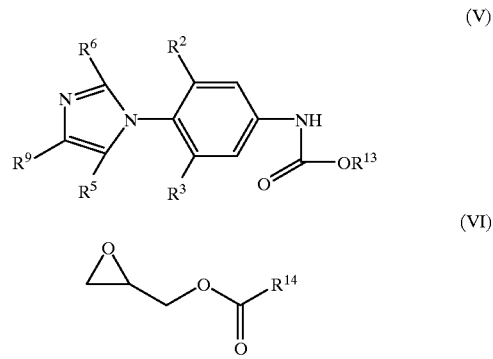

(V)

(VI)

(g) when R$^{10}$ is of the formula —N(CO$_2$R$^{15}$)CO(1–4C) alkyl [wherein R$^{15}$ is (1–4C)alkyl or benzyl], from a compound of the formula (I) or (II) wherein R$^1$ or R$^{10}$ is hydroxy;

(h) when R$^5$ or R$^{10}$ is chloro, fluoro, (1–4C) alkanesulfonyloxy or (1–4C)alkylaminocarbonyloxy, from a compound of the formula (I) or (II) wherein R$^1$ or R$^{10}$is hydroxy;

(i) when $R^1$ or $R^{10}$ is chloro, (1–4C)alkylthio or (1–4C) alkoxy, from a compound of the formula (IV); wherein $L^2$, $L^1$, X, Y, $R^2$, $R^3$, $R^5$, $R^6$ and $R^9$ are as hereinabove or hereinafter defined, and thereafter if necessary:

i) removing any protecting groups;
ii) forming a pharmaceutically acceptable salt,
iii) forming a suitable N-oxide.

The processes (a) and (c) to (i) may be performed using compounds of the formula (I) or (II) as defined hereinbefore with compounds of the formula (II) in which $R^9$ is —X—$L^2$ (or a protected version thereof—see hereinbefore and Examples for suitable protecting groups). The process (b) may then be performed using the compound in which —X—$L^2$ is unprotected. Certain values of assembled —X—Y— links in compounds of formula (I) and (II) (wherein $R^9$ is $R^4$ or protected $R^4$) are unsuitable for use with processes (a) and (c) to (i); the skilled organic chemist will recognise when this is so, and, for example, the oxazo-lidinone ring should be assembled before the —X—Y— link is assembled.

Certain intermediate compounds described hereinbefore and hereinafter, for example those in which —X—$L^2$ in a compound of formula (II) is azidomethyl are novel and are provided as a further feature of the invention.

Process (a)

Methods for converting substituents into other substituents are known in the art. For example a cyano group reduced to an amino group, a nitro group reduced to an amino group, a hydroxy group alkylated to a methoxy group, a bromo group to a cyano group, a thio group oxidised to a sulfinyl or sulfonyl group, a (1–4C)alkoxycarbonyl group converted to a carbamoyl group (see Example 27, for example) or an amino group converted to a (2–4C) alkanoylamino group (see Example 48, for example).

A linking group in one compound of the formula (I) or (II) may be converted into another linking group, for example, a —CO— link may be converted into a —CH(OH) link.

Process (b)

It will be appreciated that process (b) provides means for assembling the —X—Y— link in compounds of the formula (I). In describing the reactions suitable for this assembly the terms $L^2$—X— and —Y—$L^1$ have been used to define certain intermediate compounds, but the terms $L^2$, X, Y and $L^1$ are not necessarily strictly limited to those defined hereinbefore. Thus, for example, amide links may be established by reaction of a compound of formula (III) in which $L^2$—X— is a carboxy group (i.e. $L^2$ is —OH and X is —CO—) with a Het.—Y—$L^1$ compound wherein Y is —NH— and $L^1$ is H. The —X—Y— link in this case (—CONH—) is provided for in the definition of compounds of formula (I) hereinbefore by X as a direct bond and Y as —CONH— $(CH_2)_m$— with m is 0. Thus, process (b) includes those processes in which compounds of formula (III) and Het.—Y—$L^1$ are such that $L^2$—X— and —Y—$L^1$ (or a part thereof) are suitable to give an assembled —X—Y— link as defined hereinbefore. The skilled organic chemist will recognise from the range of assembled —X—Y— links and the description for process (b) given hereinbefore and hereinafter how such —X—Y— links may be assembled.

The coupling reaction between a compound of the formula (III) and a compound of the formula Het—Y—$L^1$ is conveniently performed in an inert solvent such as acetonitrile, dichloromethane, N,N-dimethylformamide or N,N-dimethylacetamide, at a temperature in the range 0° C. to the reflux temperature of the solvent, preferably in the range ambient to 70° C. The precise reaction conditions and the nature of the starting materials will depend upon the nature of the —X—Y— bond that is to be formed between the imidazole ring in the compound of formula (III) and the Het. group in $R^4$ or $R^9$. The skilled organic chemist will be able to select suitable starting materials and conditions to produce the range of —X—Y— bonds detailed in this specification, and non-limiting representative examples are provided in the Examples contained herein. Suitable values for the leaving groups $L^1$ and $L^2$ are provided below. For example:

Methylthio linkages (X is —$CH_2$—, Y is —S—) may be prepared by the reaction of an (activated) methylhydroxy compound (X is —$CH_2$—, $L^2$ is —OH or another suitable leaving group prepared from —OH) with a thioxo or thiol compound (—Y—$L^1$ is =S, or Y is —S—and $L^1$ is —H) in the presence of an agent such as N,N-dimethylformarnmide dineopentylacetal (DMFDMPA) which activates the —OH group for displacement and also generates an in-situ base for generating the required nucleophile.

Methylamino linkages (X is —$CH_2NH$—, Y is a direct bond) may be prepared by the reaction of a methylamino compound (X is —$CH_2NH$—, $L^2$ is —H) with, for example, a halo compound (—Y—$L^1$ is—halo, Y is a direct bond, $L^1$ is halo).

Amide (for example methylaminocarbonyl) linkages (X is —$CH_2NH$—, Y is —CO—) may be prepared by the reaction of a methylamino compound (X is —$CH_2NH$—, $L^2$ is —H) with an acid chloride compound (—Y—$L^1$ is —COCl, Y is —CO—, $L^1$ is chloro). Other amide linkages (for example carbonylamino(1–4C)alkyl and carbonylamino; X is —CONH—, Y is —$(CH_2)_n$— wherein n is 0, 1, 2 or 3) may be prepared by the reaction of an activated carboxy compound (X—$L^2$ is —$CO_2H$, $L^2$ is —OH) with an amine (—Y—$L^1$ is —$(CH_2)_nNH_2$, $L^1$ is —H), optionally in the presence of a coupling agent such as 1-(3-dimethylaminopropyl)-3-ethylcarbodiimide methiodide. Suitable activated carboxy compounds are, for example, the esters formed from the reaction of the carboxy compound with 4-nitrophenol, or 1-hydroxybenzotriazole.

Amide linkages in which the nitrogen atom of the amide bond is provided by a ring nitrogen atom in a non-aromatic Het. moiety can be prepared from a carboxy compound (X is —CO—, Y is —$(CH_2)_n$— wherein n is 0, ie. a direct bond) may be prepared by the reaction of an activated carboxy compound (X—$L^2$ is —$CO_2H$, $L^2$ is —OH) with a non-aromatic nitrogen containing Het. compound (optionally with functionalities protected, —Y— is a direct bond, —$L^1$ is —H), optionally in the presence of a coupling agent such as 1-(3-dimethylaminopropyl)-3-ethylcarbodiimide methiodide.

Amide (urea or thiourea) linkages in which —Y—$L^1$ or $L^2$—X— may form part of the final —X—Y— link may be prepared from the reaction of a compound of the formula (III) in which $L^2$—X— is an isocyanate or isothiocyanate group with a Het.—$(CH_2)_m$-amine (wherein m is 0 to 3). Alternatively, Het.—$(CH_2)_m$—NCO or Het.—$(CH_2)_m$—NCS may be reacted with a compound of the formula (III) in which $L^2$—X— is an amine group (wherein m is 0 to 3). These reactions illustrate cases in which —Y—$L^1$ or $L^2$—X— is —$(CH_2)_m$-amine, or —$(CH_2)_m$—NCO or —$(CH_2)_m$—NCS.

Similarly, sulfonamide (for example methylaminosulfonyl) linkages (X is —$CH_2NH$—, Y is —$SO_2$—) may be prepared by the reaction of a methylamino compound (X is —$CH_2NH$—, $L^2$ is —H) with a sulfonyl chloride compound (—Y—$L^1$ is —$SO_2Cl$, Y is —$SO_2$—, $L^1$ is chloro).

Ester linkages (for example methoxycarbonyl) linkages (X is —CH$_2$O—, Y is —CO—) may be prepared by the reaction of a methylhydroxy compound (X is —CH$_2$O—, L$^2$ is —H) with carboxy compound (—Y—L$^1$ is —CO$_2$H, L$^1$ is —OH) in the presence of a coupling agent such as DMFDMPA which activates the —OH group for displacement and also generates an in-situ base for generating the required nucleophile. Other ester linkages (for example carbonyloxymethyl; X is a direct bond, Y is —C(=O)O—CH$_2$—) may be prepared by the reaction of a carboxy compound (X—L$^2$ is —CO$_2$H—, L$^2$ is —OH) with a methylhydroxy compound (—Y—L$^1$ is —CH$_2$OH, L$^1$ is —H) in the presence of a coupling agent such as dimethylarninopyridine and dicyclohexylcarbodiimide.

Alkylene chain linkages (for example X is methylene, —CH$_2$—) to a ring nitrogen atom in a non-aromatic Het. moiety can be prepared, for example, by reaction of a methylhydroxy compound (X is —CH$_2$—, L$^2$ is —OH) with a non-aromatic Het. compound (optionally with functionalities protected, —Y— is a direct bond, —L$^1$ is —H), optionally in the presence of a coupling agent such as N,N-dimethylformamide dineopentylacetal (DMFDMPA) which activates the —OH group for displacement and also generates an in-situ base for generating the required nucleophile.

Direct bond linkages (in which the Het. moiety of R$^4$ is linked directly to the imidazole ring in the compound of formula (III)) may be formed, for example by reaction of a compound of formula (III) in which L$^2$—X— is formyl (L$^2$ is =O here) with a compound capable of forming a Het. moiety incorporating the formyl carbon atom as part of the Het. ring. Thus, as illustrated in Examples 81 and 82, a diamine (such as 2-aminoaniline) may be reacted with the formyl compound (to give a benzimidazole moiety as Het., directly C-linked to the imidazole ring of the product compound).

The reaction between a compound of the formula (III) and a compound capable of forming a Het. moiety may be performed, for example, using a compound of the formula (III) in which L$^2$—X— is azidomethyl to form a 1,2,3-triazole ring upon reaction with ethyl propiolate. In this case L$^2$ is not a leaving group as all three nitrogen atoms of the azido group are incorporated in the 1,2,3-triazole ring.

Compounds of the formula (III) may be prepared by using the processes described in this specification, and as, for example, illustrated in the accompanying Examples. Thus, for example, a compound of the formula (III) in which L$^2$—X— is hydroxymethyl may be prepared using process (f), ie. from a compound of the formula (V) in which R$^9$ is hydroxymethyl (or protected hydroxymethyl). This hydroxymethyl group may be modified to a azidomethyl group, which may then be reduced to an aminomethyl group (see, for example, Example 19 preparation of intermediate). Such modifications are known in the art. The hydroxymethyl group may also be oxidised to an alkanoyl (eg. formyl) group, and further oxidised to a carboxy group, using known oxidising techniques and reagents.

The preparation of compounds of the formula Het.—Y—L$^1$, Het.—(CH$_2$)$_m$-amine, Het.—(CH$_2$)$_m$—NCO or Het.—(CH$_2$)$_m$—NCS (wherein m is 0 to 3) and of compounds capable of forming a Het. moiety, is within the skill of the skilled organic chemist, or are cornmercially available.

Process (c)

When R$^a$ is (1–4C)alkyl, the group —C(=O)(1–4C)alkyl may be introduced into a compound of the formula (I) or (II) wherein R$^1$ or R$^{10}$ is amino by standard acetylation procedures. For example, the amino group may be acetylated to give an acetamido group using the Schotten-Baumann procedure i.e. reacting the compound of the formula (I) or (II) wherein R$^1$ or R$^{10}$ is amino with acetic anhydride in aqueous sodium hydroxide and THF in a temperature range of 0° C. to 60° C. , preferably between 0° C. and ambient temperature. The acylation may be carried out in situ following the catalytic hydrogenation of a compound of the formula (I) or (II) wherein R$^1$ or R$^{10}$ is azido, by performing the hydrogenation in the presence of acetic anhydride (for example using similar methods to those used in example 4).

When R$^a$ is hydrogen, the —CHO group may be introduced into the compound of the formula (I) or (II) wherein R$^1$ or R$^{10}$ is amino (amino compound) by reacting the latter compound in formic acetic anhydride, in an inert organic solvent such as THF, in a temperature range of 0° C. to ambient temperature, or by reacting it with ethyl formate in an inert organic solvent in the temperature range of 50–100° C.

When R$^a$ is (1–4C)alkoxy, the —COO(1–4C)alkyl group may be introduced into the amino compound by reacting the latter compound with (1–4C)alkyl chloroformate, in the presence of an organic base such as triethylamine, in an organic solvent such as dichloromethane and in a temperature range of 0° C. to ambient temperature.

When R$^a$ is chloromethyl, dichloromethyl, cyanomethyl or methoxymethyl, the —C(=O)R$^a$ group may be introduced into the amino compound by reacting the latter compound with the appropriate acid chloride under standard conditions. The acid chloride may be prepared from the appropriate acid. When R$^a$ is acetyimethyl, the —C(=O)R$^a$ group may be introduced into the amino compound by reacting the latter compound with diketene, in an inert organic solvent such as THF, in a temperature range of 0° C. to ambient temperature.

Alternatively, the amino compound may be reacted with the appropriate acid anhydride, in dichloromethane or THF, in the presence of an organic base such as triethylamine and in a temperature range of 0° C. to ambient temperature, or the amino compound may be reacted with the appropriate acid in the presence of 1-(3-dimethylaminopropyl)-3-ethylcarbodiimide hydrochloride and an organic base such as triethylamine, in an organic solvent such as dichloromethane, in a temperature range of 0° C. to ambient temperature.

Process (d)

Suitable reducing agents for reducing azido to amino in a compound of the formula (I) or (II) include triethylamine/hydrogen sulfide, triphenylphosphine or phosphate ester, or hydrogen in the presence of a catalyst. More specifically the reduction of the azido group may be carried out by heating it in an aprotic solvent, such as 1,2-dimethoxyethane, in the presence of P(OMe)$_3$ and subsequently heating in 6N aqueous hydrochloric acid, or reacting it with hydrogen in the presence of palladium on carbon in a protic such as DMF or ethyl acetate. For further details on the reduction of azides to amines see U.S. Pat. No. 4,705,799. The azido compound may be reduced and converted to a compound of the formula (I) or (II), wherein R$^1$ or R$^{10}$ is acetamido, in situ using acetic anhydride in DMF.

Process (e)

A compound of the formula (I) or (II) wherein R$^1$ or R$^{10}$ is azido may be prepared, for example, by reacting a compound of the formula (IV) with sodium azide in an inert solvent such as DMF in a temperature range of ambient to 100° C., normally in the region of 75° C.–85° C., A compound of the formula (IV) may be prepared by converting the hydroxy group in a compound of the formula (I) or (II) wherein $R^1$ or $R^{10}$ is hydroxy into a tosyloxy or mesyloxy group by standard methods known in the art. For example, by reacting a compound of the formula (I) or (II) wherein $R^1$ or $R^{10}$ is hydroxy with tosyl chloride, mesyl chloride or a chlorophosphate ester in the presence of a mild base such as triethylamine, or pyridine.

Process (f)

Compounds of the formulae (V) and (VI) are conveniently reacted together in the presence of a strong base such as butyl lithium, lithium bistrimethylsilylamide, sodium hydride, or lithium diisopropylamide. The reaction is conveniently carried out in an inert solvent such as tetrahydrofuran (THF), dimethylformamide (DMF), N,N$^1$-dimethylpropyleneurea (DMPU) or N-methylpyrrolidone in a temperature range of −78° C. to −50° C. for the deprotonation and cyclisation. Suitable values for $R^{13}$ include ethyl and benzyl and suitable values for $R^{14}$ include ethyl and n-propyl, preferably n-propyl.

A compound of the formula (V) is conveniently prepared by reacting a chloroformate of the formula (ClCOOR$^{13}$) with a compound of the formula (VA):

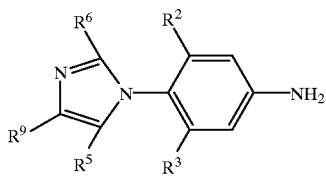

(VA)

wherein $R^2$, $R^3$, $R^5$, $R^6$ and $R^9$ are as hereinabove defined.
The reaction is conveniently carried out in the presence of an inorganic or organic base such as sodium bicarbonate or an amine base such as dimethylaniline, the former in a solvent such as acetone/water and the latter in an organic solvent such as TRF, toluene, DMF or acetonitrile.

A compound of the formula (VA) may be prepared by reducing a compound of the formula (VB):

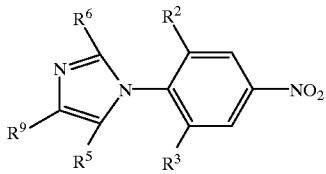

(VB)

wherein $R^2$, $R^3$, $R^5$, $R^6$ and $R^9$ are as hereinabove defined.

Many reduction methods suitable for the reduction of a nitro to an amino group are known in the art, for example catalytic hydrogenation, metal reductions or with reducing agents such as sodium hydrosulfite. Suitable catalysts in catalytic hydrogenation include Raney nickel, platinum metal and its oxide, rhodium, palladium-on-charcoal and Wilkinson's catalyst RhCl (Ph$_3$P)$_3$. Catalyst hydrogenation is conveniently carried out in the temperature range 0° C.–50° C., but preferably at ambient temperature at slightly above atmospheric pressure.

A compound of the formula (VB) is conveniently prepared by reacting together compounds of the formulae (VC) and (VD):

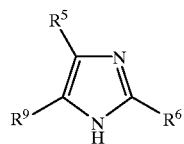

(VC)

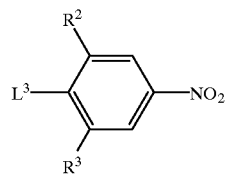

(VD)

wherein $R^2$, $R^3$, $R^5$, $R^6$ and $R^9$ are as hereinabove defined and $L^3$ is a leaving group, preferably halo and in particular fluoro.

The reaction between compounds of the formulae (VC) and (VD) is carried out in the presence of an organic or inorganic base such as sodium bicarbonate, potassium carbonate or an amine base such as diisopropylethylamine, in an inert solvent such as acetonitrile, DMF, DMPU or N-methylpyrrolidone, in a temperature range of 50° C.–150° C.

Compounds of the formula (VC) may be prepared by introducing substituents into or modifying substituents in a known optionally substituted imidazole ring. Such conversions are well known to the skilled chemist, for example a cyano group may be hydrolysed to a carboxy group which in turn may be converted to a carbamoyl or alkoxycarbonyl group or reduced to a hydroxymethyl group; an amino group may be acylated to an alkanoylamino group; a thio group may be alkylated to an alkylthio group which in turn may be oxidised to an alkylsulfinyl or alkylsulfonyl group and a hydroxyalkyl group may be alkylated to an alkoxyalkyl group.

Alternatively compounds of the formula (VC) may be prepared using the methods described in Houben-Weyl, Methoden der organischen Chemie, Heterarene III Teil 3, ed E Schaumann (1994), or The Chemistry of Heterocyclic Compounds, Vol 6, Part 1 "Imidazole and its Derivatives" (1953).

Process (g)

A compound of the formula (II) wherein $R^{10}$ is of the formula —N(CO$_2$R$^{15}$)CO(1–4C)alkyl is conveniently prepared by reacting a compound of the formula (I) and (II) wherein $R^1$ or $R^{10}$ is hydroxy with an amide of the formula HN(CO$_2$R$^{15}$)CO(1–4C)alkyl under Mitsunobu conditions. For example, in the presence of tri-n-butylphosphine and 1,1'-(azodicarbonyl)dipiperndine in an organic solvent such as THF, and in the temperature range 0° C.–60° C., but preferably at ambient temperature. Details of analogous Mitsunobu reactions are contained in Tsunoda et al., Tet. Letts., 34, 1639, (1993). Amides of the formula HN(CO$_2$R$^{15}$)CO(1–4C)alkyl may be prepared by standard procedures of organic chemistry which are within the ordinary skill of an organic chemist.

Process (h)

A compound of the formula (I) or (II) wherein $R^1$ or $R^{10}$ is fluoro may be prepared by reacting a compound of the formula (I) or (II) wherein $R^1$ or $R^{10}$ is hydroxy (hydroxy compound) with a fluorinating agent such as diethylaminosulfur trifluoride in an organic solvent such as dichloromethane in the temperature range of 0° C. to ambient temperature.

When $R^1$ or $R^{10}$ is chloro, the compound of the formula (I) or (II) may be formed by reacting the hydroxy compound with a chlorinating agent. For example, by reacting the hydroxy compound with sulfinyl chloride in a temperature range of ambient temperature to reflux, optionally in a chlorinated solvent such as dichloromethane or by reacting the hydroxy compound with carbon tetrachloride/triphenyl phosphine in dichloromethane, in a temperature range of 0° C. to ambient temperature.

The (1–4C)alkanesulfonyloxy compound may be prepared by reacting the hydroxy compound with (1–4C) alkanesulfonyl chloride in the presence of a mild base such as triethylamine or pyridine.

The (1–4C)alkylaminocarbonyloxy compound may be prepared by reacting the hydroxy compound with (1–4C) alkyl cyanate in an organic solvent such as THF or acetonitrile, in the presence of triethylamine, in a temperature range of 0° C. to 50° C.

Process (i)

A compound of the formula (I) or (II) wherein $R^1$ or $R^{10}$ is chloro may also be prepared from a compound of the formula (IV), by reacting the latter compound with lithium chloride and crown ether, in a suitable organic solvent such as THF, in a temperature range of ambient temperature to reflux. A compound of the formula (I) or (II) wherein $R^1$ or $R^{10}$ is (1–4C)alkylthio or (1–4C)alkoxy may be prepared by reacting the compound of the formula (IV) with sodium thio(1–4C)alkoxide or sodium (1–4C)alkoxide respectively, in an alcohol or THF, in a temperature range of 0° C. to reflux.

Suitable N-oxides of compounds of the formula (I) or (II) may be prepared directly from a corresponding parent compound of the formula (I) or (II) using techniques well known to the ordinary skilled organic chemist, such as, for example, using a peracid (such as m-chloroperbenzoic acid) or perphthalic acid in a suitable solvent (such as dioxan or a mixture of water and THF) at a suitable temperature (such as ambient temperature). The preparation of suitable N-oxides by assembly from suitable N-oxide starting materials and the use of the processes described in this specification is within the skill of the ordinary skilled organic chemist, and is illustrated by, for example, Example 5.

When an optically active form of a compound of the formula (I) is required, it may be obtained by carrying out one of the above procedures using an optically active starting material or by resolution of a racemic form of the compound or intermediate using a standard procedure.

According to a further feature of the invention there is provided a compound of the formula (I), or a pharmnaceutically-acceptable salt thereof, for use in a method of treatment of the human or animal body by therapy, According to a further feature of the present invention there is provided a method for producing an antibacterial effect in a warm blooded animal, such as man, in need of such treatment, which comprises administering to said animal an effective amount of a compound of the present invention, or a pharmaceutically-acceptable salt thereof.

The invention also provides the use of a compound of the present invention, or a pharmaceutically-acceptable salt thereof, for use as a medicament; and the use of a compound of the present invention, or a pharmaceutically-acceptable salt thereof, in the manufacture of a novel medicament for use in the production of an antibacterial effect in a warm blooded animal, such as man.

In order to use a compound of the formula (I) or a pharmaceutically-acceptable salt thereof for the therapeutic treatment of mammals including humans, in particular in treating infection, it is normally formulated in accordance with standard pharmaceutical practice as a pharmaceutical composition.

Therefore in another aspect the present invention provides a pharmaceutical composition which comprises a compound of the formula (I) or a pharmnaceutically-acceptable salt thereof and a pharmaceutically-acceptable diluent or carrier.

The pharmaceutical compositions of this invention may be administered in standard manner for the disease condition that it is desired to treat, for example by oral, rectal or parenteral administration. For these purposes the compounds of this invention may be formulated by means known in the art into the form of, for example, tablets, capsules, aqueous or oily solutions or suspensions, (lipid) emulsions, dispersible powders, suppositories, ointments, creams, drops and sterile injectable aqueous or oily solutions or suspensions.

In addition to the compounds of the present invention the pharmaceutical composition of this invention may also contain or be co-administered with one or more known drugs selected from other clinically useful antibacterial agents (for example β-lactams or aminoglycosides). These may include penicillins, for example oxacillin or flucloxacillin, carbapenems (for example meropenem or imipenem) and monobactams (for example aztreonam) to broaden the therapeutic effectiveness. Compounds of this invention may also contain or be co-administered with bactericidal/permeability-increasing protein product (BPI) or efflux pump inhibitors to improve activity against gram negative bacteria and bacteria resistant to antimicrobial agents.

A suitable pharmaceutical composition of this invention is one suitable for oral administration in unit dosage form, for example a tablet or capsule which contains between 100 mg and 1 g of the compound of this invention.

In another aspect a pharmaceutical composition of the invention is one suitable for intravenous, subcutaneous or intramuscular injection.

Each patient may receive, for example, a daily intravenous, subcutaneous or intramuscular dose of 5 mgkg-$^1$ to 20 mgkg-$^1$ of the compound of this invention, the composition being administered 1 to 4 times per day. The intravenous, subcutaneous and intramuscular dose may be given by means of a bolus injection. Alternatively the intravenous dose may be given by continuous infusion over a period of time. Alternatively each patient will receive a daily oral dose which is approximately equivalent to the daily parenteral dose, the composition being administered 1 to 4 times per day.

Antibacterial Activity

The pharmaceutically acceptable compounds of the present invention are useful antibacterial agents having a good spectrum of activity in vitro against standard Gram-positive organisms, which are used to screen for activity against pathogenic bacteria. Notably, the pharmaceutically acceptable compounds of the present invention show activity against enterococci, pneumococci and methicillin resistant strains of *S. aureus* and coagulase negative staphylococci. The antibacterial spectrum and potency of a particular compound may be determined in a standard test system.

The antibacterial properties of the compounds of the invention may also be demonstrated in vivo in conventional tests.

The following results were obtained on a standard in vitro test system. The activity is described in terms of the minimum inhibitory concentration (MIC) determined by the agar-dilution technique with an inoculum size of $10^4$ CFU/spot.

The organisms were tested on a standard semi-defined susceptability test medium (IsoSensitest agar), using an inoculum of $10^4$ CFU/spot and an incubation temperature of 37° C. for 24 hours.

| Organism | MIC (μg/ml) Example 43 |
|---|---|
| *Staphylococcus aureus:* | |
| Oxford | 0.125 |
| Novb. Res | 0.25 |
| MRQR | 1.0 |
| Coagulase Negative Staphylococcus | |
| MS | 0.06 |
| MR | 0.25 |
| *Streptococcus pyogenes* | |
| C203 | 0.125 |
| *Enterococcus faecalis* | 0.5 |
| *Bacillus subtilis* | 0.25 |

Novb. Res=Novobiocin resistant

MRQR=methicillin resistant quinolone resistant

MR=methicillin resistant

The invention is now illustrated by the following Examples in which unless otherwise stated:

i) evaporations were carried out by rotary evaporation in vacuo and work-up procedures were carried out after removal of residual solids by filtration;

(ii) operations were carried out at ambient temperature, that is in the range 18–26° (temperatures are in degrees Celsius ° C.) and in air unless otherwise stated, or unless the skilled person would otherwise work under an inert atmosphere;

(iii) column chromatography (by the flash procedure) was performed on Merck Kieselgel silica (Art. 9385) unless otherwise stated;

(iv) yields are given for illustration only and are not necessarily the maximum attainable;

(v) the structures of the end-products of the formula I were confirmed by NMR and mass spectral techniques [proton magnetic resonance spectra were determined in DMSO-D6 unless otherwise stated using a Varian Gemini 2000 spectrometer operating at a field strength of 300 MHz, or a Bruker AM250 spectrometer operating at a field strength of 250 MHz; chemical shifts are reported in parts per million downfield from tetramethysilane as an internal standard (δ scale) and peak multiplicities are shown thus: br, broad; s, singlet; d, doublet; dd, doublet of doublets; t, triplet, m, multiplet; fast-atom bombardment (FAB) mass spectral data were obtained using a Platform spectrometer (supplied by Micromass) run in electrospray and, where appropriate, either positive ion data or negative ion data were collected];

(vi) intermediates were not generally fully characterised and purity was in general assessed by thin layer chromatographic, infra-red (IR), mass spectral (MS) or NMR analysis;

(vii) in which the following abbreviations may be used:

| MPLC | is medium pressure chromatography |
|---|---|
| TLC | is thin layer chromatography |
| DMSO | is dimethylsulfoxide |
| $CDCl_3$ | is deuterated chloroform |
| MS | is mass spectroscopy |
| ESP | is electrospray |
| CI | is chemical ionization |
| DMF | is N,N-dimethylformamide |
| THF | is tetrahydrofuran | and (viii) when product acetamide structures are shown the pharmnaceutically-active enantiomer ((5S)-methylacetamide) is shown.

EXAMPLE 1

N-[(5S)-3-(3-Fluoro-4-(4-pyrimidin-2-ylthiomethylimidazol-1-yl)phenyl)-2-oxooxazolidin-5-ylmethyl]acetamide N-[(5S)-3-(3-Fluoro-4-(4-hydroxymethylimidazol-1-yl)phenyl)-2-oxooxazolidin-5-yl-methyl]acetamide (174 mg, 0.5 mM) and pyrimidine-2-thione (112 mg, 1 mM) were suspended in dry acetonitrile (20 ml), and N,N-dimethylformamide dineopentyl acetal (462 mg, 2 mM) added. The mixture was heated to reflux for 6 hours giving a solution. Solvent was evaporated, the residue dissolved in dichloromethane, and subjected to mplc on silica, eluting with a gradient increasing in polarity from 0 to 20% methanol in dichloromethane. Relevant fractions were combined and evaporated to give the title product (204 mg) as a gum.

MS (ESP): 443 (MH$^+$) for $C_{20}H_{19}FN_6O_3S$; NMR (DMSO-D6) δ: 1.81 (s, 3H); 3.41 (t, 2H); 3.75 (dd, 1H); 4.13 (t, 1H); 4.34 (s, 2H); 4.74 (m, 1H); 7.21 (t, 1H); 7.41 (dd, 1H); 7.46 (s, 1H); 7.63 (t, 1H); 7.71 (dd, 1H); 7.94 (t, 1H); 8.23 (brt, 1H); 8.64 (d, 2H).

The intermediate for this compound was prepared as follows:

3-Fluoro-4-(4-hydroxymethylimidazol-1-yl)nitrobenzene 3,4-Difluoro-nitrobenzene (23.85 g) was dissolved in acetonitrile (180 ml), followed by 4-hydroxymethylimidazole (14.7 g) and ethyldiisopropylamine (65.2 ml). The mixture was stirred and heated to reflux for 2 days. After cooling, acetonitrile was evaporated and the residue was shaken with a mixture of methyl t-butyl ether (200 ml) and water (100 ml), and the solid filtered. After washing with a mixture of methyl t-butyl ether (50 ml) and water (25 ml), the solid was dried in vacuo at 60° C. overnight, to give product (26.8 g) mp 157–159° C.

MS (CI): 238 (MH$^+$) for $C_{10}H_8FN_3O_3$; NMR (DMSO-D6) δ: 4.57 (d, 2H); 5.18 (t, 1H); 7.66 (t, 1H); 8.11 (t, 1H); 8.28 (t, 1H); 8.35 (dm, 1H); 8.54 (dd, 1H).

3-Fluoro-4-(4-t-butyldimethylsilyloxymethylimidazol-1-yl)nitrobenzene

3-Fluoro-4-(4-hydroxymethylimidazol-1-yl)nitrobenzene (26.7 g) and imidazole (15.3 g) were suspended in dry N,N-dimethylformnamide (190 ml) and stirred under argon on an ice-bath. t-Butyldimethylsilylchloride (25.5 g) was added in one portion, and stirring continued at ice temperature for 30 minutes, then at ambient temperature overnight. Solvent was evaporated in vacuo at 30° C., the residue diluted with water (200 ml) and extracted into ethyl acetate (700 ml). After washing with water (2×300 ml), brine, and drying over magnesium sulfate, solvent was evaporated (finally on high vacuum) to give an oil which solidified (39.2 g). This was used in the next stage with no further purification.

NMR (DMSO-D6) δ: 0.00 (s, 6H); 0.82 (s, 9H); 4.55 (s, 2H); 7.44 (m, 1H); 7.89 (t, 1H); 8.06 (t, 1H); 8.14 (dm, 1H); 8.33 (dd, 1H).

1-Amino-4-(4-t-butyldimethylsilyloxymethylimidazol-1-yl)fluorobenzene

3-Fluoro-4-(4-t-butyldimethylsilyloxymethylimidazol-1-yl)nitrobenzene (39.0 g) was dissolved in a mixture of methanol (220 ml) and tetrahydrofuran (890 ml) and stirred under argon in an ice-bath. Ammonium formate (35.2 g) was added, followed by 10% palladium on charcoal (1.6 g), and the mixture allowed to warm to ambient temperature. Stirring was continued for 2 days. TLC showed a trace of remaining starting material, so farther palladium catalyst (0.5 g) was added, and more ammonium formate (35 g) in portions over 6 hours, before leaving to stir overnight, giving essentially one spot as product. The catalyst was filtered off on celite, the cake washed well with methanol/tetrahydrofuran, and filtrates evaporated to dryness. The residue was partitioned between ethyl acetate (700 ml) and water (200 ml), the organic layers washed with water, brine, and dried over magnesium sulfate. Evaporation gave an oil (36 g), used in the next stage with no further purification.

MS (ES): 322 (MH$^+$) for $C_{16}H_{24}FN_3OSi$; NMR (DMSO-D6) δ: 0.04 (s, 6H); 0.85 (s, 9H); 4.56 (s, 2H); 5.63 (s, 2H); 6.45 (dd, 1H); 6.48 (dd, 1H); 7.12 (t, 1H); 7.13 (s, 1H); 7.69 (s, 1H).

1-benzyloxycarbonylamino-4-(4-t-butyldimethylsilyloxymethylimidazol-1-yl)fluorobenzene 1-Amino-4-(4-t-butyldimethylsilyloxymethylimidazol-1-yl)fluorobenzene (36.1 g) was dissolved in dry dichloromethane (450 ml), treated with pyridine (11.3 ml), then stirred under argon while cooling to −20° C. Benzyl chloroformate (17.7 ml) in dichloromethane (50 ml) was added dropwise, maintaining the temperature. The mixture was then allowed to warm to ambient temperature over 1 hour, then stirred for a further 1.5 hours. The mixture was diluted with aqueous sodium bicarbonate (250 ml), and the organic layer separated. A further extraction with dichloromethane (200 ml) was made, the combined organic layers dried over magnesium sulfate, and solvent evaporated. The resulting oil was re-evaporated with toluene, and purified by chromatography on silica (500 g) in a sinter column, eluting with a gradient from $CH_2Cl_2$ to 50% EtOAc in $CH_2Cl_2$. Evaporation, then re-evaporation with toluene gave solid product (51 g).

MS (ES): 456 (MH$^+$) for $C_{24}H_{30}FN_3O_3Si$; NMR (DMSO-D6) δ: 0.00 (s, 6H); 0.77 (s, 9H); 4.53 (s, 2H); 5.11 (s, 2H); 7.24–7.40 (complex, 7H); 7.46 (t, 1H); 7.53 (dd, 1H); 7.79 (s, 1H); 10.10 (s, 1H).

(5R)-3-(4-(4-t-Butyldimethylsilyloxymethylimidazol-1-yl)-3-fluorophenyl)-5-hydroxymethyloxazolidin-2-one t-Butanol (6.1 g) in dry tetrahydrofuran (50 ml) was stirred under argon at −10°. n-Butyllithium in isohexane (1.6M, 41.3 ml) was added dropwise, the mixture stirred for 10 minutes, then cooled to −70°. A solution of 1-benzyloxycarbonylamino-4-(4-t-butyldimethylsilyloxymethylimidazol-1-yl)fluorobenzene (25.0 g) in dry tetrahydrofuiran (150 ml) was added dropwise over 20 minutes, then stirred for 20 minutes at −70° C. (R)-glycidylbutyrate (9.5 g) in tetrahydrofuiran (10 ml) was added dropwise over 10 minutes, keeping the temperature below −60° C. Stirring was continued overnight, allowing the temperature to rise to ambient. Saturated sodium bicarbonate solution (200 ml) was added, and the mixture extracted with ethyl acetate (500 and 200 ml). After drying over magnesium sulfate and evaporation the residue was purified by chromatography on silica, eluting with a gradient from dichloromethane to 20% MeOH in dichloromethane. Relevant fractions were combined and evaporated to give a gum (20.5 g).

MS (ES): 422 (MH$^+$) for $C_{20}H_{28}FN_3O_4Si$; NMR (DMSO-D6) δ: 0.02 (s, 6H); 0.81 (s, 9H); 3.49 (brd, 1H); 3.63 (brd, 1H); 3.80 (dd, 1H); 4.06 (t, 1H); 4.55 (s, 2H); 4.68 (s, 1H); 5.14 (brs, 1H); 7.30 (s, 1H); 7.41 (dm, 1H); 7.58 (t, 1H); 7.68 (dd, 1H); 7.85 (t, 1H).

(5R)-3-(4-(4-t-Butyldimethylsilyloxymethylimidazol-1-yl)-3-fluoro-2henyl)-5-methanesulfonyloxymethyloxazolidin-2-one (5R)-3-(4-(4-t-Butyldimethylsilyloxymethylimidazol-1-yl)-3-fluoro-phenyl)-5-hydroxy-methyloxazolidin-2-one (8.0 g) was dissolved in dry dichloromethane (60 ml ) with stirring under argon in an ice-bath. Triethylamine (3.44 ml) was added, followed by dropwise addition of methanesulfonyl chloride (1.62 ml). Stirring was continued for 2 hours as the mixture warmed to ambient temperature. Aqueous sodium bicarbonate was added, the organic layer separated, and further extracted with dichloromethane. Combined extracts were dried over magnesium sulfate. Evaporation gave a gum (9.4 g), which was dried under high vacuum, and used as such in the next stage.

NMR (DMSO-D6) δ: 0.07 (s, 6H); 0.88 (s, 9H); 3.46 (s, 3H); 3.88 (dd, 1H); 4.25 (t, 1H); 4.49 (m. 2H); 4.61 (s, 2H); 5.06 (m, 1H); 7.36 (s, 1H); 7.46 (dm, 1H); 7.67 (t, 1H); 7.84 (dd, 1H); 7.94 (t, 1H).

(5R)-5-Azidomethyl-3-(4-(4-t-butyldimethylsilyloxymethylimidazol-1-yl)-3-fluorophenyl)-oxazolidin-2-one ($^5$R)-3-(4-(4-t-Butyldimethylsilyloxymethylimidazol-1-yl)-3-fluorophenyl)-5-methanesulfonyloxymethyloxazolidin-2-one (13.6 g) was dissolved in dry N,N-dimethylformamide (110 ml). Sodium azide (3.53 g) was added, and the mixture was heated at 80° C. for 3.5 hours. The mixture was cooled, diluted with water (1.1 L) containing sodium bicarbonate (2 g), and extracted with ethyl acetate (2×800 ml). Combined organics were washed with water (2×300 ml), then brine, and dried over magnesium sulfate. The solution was evaporated to a small volume (~100 ml), and insolubles filtered. The ethyl acetate soluble material was columned on silica (100 g), eluting with ethyl acetate. Product fractions were combined and evaporated to give a gum (10.0 g).

MS (ES): 447 (MH$^+$) for $C_{20}H_{27}FN_6O_3Si$; NMR (DMSO-D6) δ: 0.08 (s, 6H); 0.87 (s, 9H); 3.71 (dd, 1H); 3.79 (dd, 1H); 3.84 (dd, 1H); 4.20 (t, 1H); 4.61 (s, 2H); 4.93 (m, 1H); 7.36 (s, 1H); 7.46 (dm, 1H); 7.65 (t, 1H); 7.75 (dd, 1H); 7.93 (t, 1H).

N-[(5S)-3-(4-(4-t-Butyldimethylsilyloxymethylimidazol-1-yl)-3-fluorophenyl)-2-oxooxazolidin-5-ylmethyl]acetamide To (5R)-5-azidomethyl-3-(4-(4-t-butyldimethylsilyloxymethylimidazol-1-yl)-3-fluorophenyl)oxazolidin-2-one(10.0 g) in ethyl acetate (560 ml) was added triethylamine (13.3 ml), acetic anhydride (4.5 ml), and palladium catalyst (10% on charcoal, 1.5 g), and the mixture hydrogenated at ambient temperature for 17 hours. The mixture was filtered through celite, the celite washed well with ethyl acetate, and the organic layer stirred with a saturated solution of sodium bicarbonate (100 ml) at ambient temperature for 1 hour. The organic layer was separated, dried over magnesium sulfate, and evaporated. Crude product (15 g, from two batches) was dissolved in dichloromethane and chromatographed on silica, eluting with a gradient from dichloromethane (100%) to 10% methanol in dichloromethane. Product fractions were combined to give a gum (12.3 g).

MS (ES): 463 (MH⁺) for $C_{22}H_{31}FN_4O_4Si$; NMR (DMSO-D6) δ: 0.00 (s, 6H); 0.81 (s, 9H); 1.77 (s, 3H); 3.36 (t, 2H); 3.71 (dd, 1H); 4.08 (t, 1H); 4.54 (s, 2H); 4.77 (m, 1H); 7.29 (s, 1H); 7.38 (dm, 1H); 7.59 (t, 1H); 7.64 (dd, 1H); 7.87 (t, 1H); 8.18 (brt, 1H).

N-[(5S)-3-(3-Fluoro-4-(4-hydroxymethylimidazol-1-yl)nhenyl)-2-oxooxazolidin-5-yl-methyl]acetamide N-[(5S)-3-(4-(4-t-Butyldimethylsilyloxymethylimidazol-1-yl)-3-fluorophenyl)-2-oxooxazolidin-5-ylmethyl]acetamide (6.0 g) was dissolved in a mixture of acetic acid (60 ml), tetrahydrofuran (20 ml) and water (20 ml), and left to stir overnight at ambient temperature. Solvents were evporated at 40° in vacuo to give a gum. This was dissolved in dichloromethane (25 ml), and dry diethyl ether (100 ml) stirred in. The precipitate was triturated and stirred until properly solid, then filtered, washed with ether, and dried in vacuo to give product (3.7 g).

MS (ES): 349 (MH⁺) for $C_{16}H_{17}FN_4O_4$; NMR (DMSO-D6) δ: 1.84 (s, 3H); 3.37 (t, 2H); 3.78 (dd, 1H); 4.16 (t, 1H); 4.39 (s, 2H); 4.77 (m, 1H); 4.97 (brs, 1H); 7.34 (s, 1H); 7.45 (dm, 1H); 7.66 (t, 1H); 7.71 (dd, 1H); 7.91 (t, 1H); 8.22 (brt, 1H).

EXAMPLE 2

N-[(5S)-3-(3-Fluoro-4-(4-(1-methylimidazole-2-thiomethyl)imidazol-1-yl)phenyl)-2-oxooxazolidin-5-ylmethyl]acetamide The title product (200 mg) was prepared as Example 1, but starting from 1-methylimidazole-2-thione (228 mg, 2 mM), and heating for 2 hours.

MS (ESP): 445 (MH⁺) for $C_{20}H_{21}FN_6O_3S$; NMR (DMSO-D6) δ: 1.81 (s, 3H); 3.41 (t, 2H); 3.47 (s, 3H); 3.76 (dd, 1H); 4.11 (s, 2H); 4.15 (t, 1H); 4.74 (m, 1H); 6.94 (d, 1H); 7.21 (m, 2H); 7.41 (dd, 1H); 7.58 (t, 1H); 7.69 (dd, 1H); 7.94 (t, 1H); 8.23 (brt, 1H).

EXAMPLES 3–7

Using essentially the method and scale of Example 1, but starting from the listed thione or thiol, and using 6 equivalents of N,N-dimethylformamide dineopentyl acetal, the following compounds were prepared.

| Example | Product | Starting material | Footnotes |
|---|---|---|---|
| 3 | | | 1 |
| 4 | | | 2 |
| 5 | | | 3 |

-continued

| Example | Product | Starting material | Foot notes |
|---------|---------|-------------------|------------|
| 6 | | | 4 |
| 7 | | | 5 |

Footnotes
1 MS(ESP): 463 (MH$^+$) for $C_{19}H_{19}FN_6O_3S_2$ NMR(DMSO-D6) δ: 1.82(s, 3H); 2.66(s, 3H); 3.41(t, 2H); 3.76(dd, 1H); 4.14(t, 1H); 4.46(s, 2H); 4.75(m, 1H); 7.42(dd, 2H); 7.49(s, 1H); 7.64(t, 1H); 7.71(dd, 1H); 7.97(s, 1H); 8.22(brt, 1H).
2 MS(ESP): 442(MH$^+$) for $C_{21}H_{20}FN_5O_3S$ NMR(DMSO-D6) δ: 1.82(s, 3H); 3.41(t, 2H); 3.76(dd, 1H); 4.12(t, 1H); 4.28(s, 2H); 4.75(m, 1H); 7.37(dd, 2H); 7.42(dd, 1H); 7.51(s, 1H); 7.63(t, 1H); 7.71(dd, 1H); 7.95(t, 1H); 8.22(brt, 1H); 8.35(d, 2H).
3 MS(ESP): 458(MH$^+$) for $C_{21}H_{20}FN_5O_4S$ NMR (DMSO-D6) δ: 1.82(s, 3H); 3.41(t, 2H); 3.76(dd, 1H); 4.14(t, 1H); 4.17(s, 2H); 4.75(m, 1H); 7.17(td, 1H); 7.34(td, 1H); 7.42(dd, 1H); 7.53(s, 1H); 7.63(t, 1H); 7.65(dd, 1H); 7.71(dd, 1H); 7.96(t, 1H); 8.21(brt, 1H); 8.27(dd, 1H).
4 8 Equivalents of N,N-dimethylformamide dineopentyl acetal used. MS(ESP): 519(MH$^+$) for $C_{21}H_{23}FN_8O_3S_2$ NMR(DMSO-D6) δ: 1.82(s, 3H); 2.96(s, 3H); 3.10(s, 3H); 3.41(t, 2H); 3.76(dd, 1H); 4.14(t, 1H); 4.22(s, 2H); 4.74(m, 1H); 7.42(dd, 1H); 7.45(s, 1H); 7.63(t, 1H); 7.71(dd, 1H); 7.95(t, 1H); 8.15(s, 1H); 8.22(brt, 1H).
5 3 Equivalents of N,N-dimethylformamide dineopentyl acetal used, and chromatography gradient from 0 to 10% methanol in dichloromethane.
MS(ESP): 445(MH$^+$) for $C_{21}H_{21}FN_4O_4S$ NMR(DMSO-D6) δ: 1.83(s, 3H); 3.41(t, 2H); 3.63(s, 2H); 3.77(dd, 1H); 3.80(s, 2H); 4.16(t, 1H); 4.74(m, 1H); 6.29(m, 1H); 6.37(m, 1H); 7.38(s, 1H); 7.43(dd, 1H); 7.57(d, 1H); 7.66(t, 1H); 7.71(dd, 1H); 7.92(m, 1H); 8.23(brt, 1H).

EXAMPLES 8–11

Using essentially the method and scale of Example 1, but starting from the listed thione, and using 6 equivalents of N,N-dimethylformamide dineopentyl acetal, the following compounds were prepared. Separation of the isomers was achieved by chromatography on silica Mega Bond Elut® columns, eluting with a gradient increasing in polarity from 0 to 20% methanol in dichloromethane.

| Example | Product | Starting material | Foot notes |
|---------|---------|-------------------|------------|
| 8 | | | 1 |
| 9 | | | 2 |

-continued

| Example | Product | Starting material | Footnotes |
|---|---|---|---|
| 10 | (structure) | (structure) | 3 |
| 11 | (structure) | (structure) | 4 |

Footnotes
1 Isolated ratio of S:N substitution 8:1 MS(ESP): 446(MH$^+$) for $C_{19}H_{20}FN_7O_3S$ NMR(DMSO-D6) δ: 1.82(s, 3H); 3.41(t, 2H); 3.48 (s, 3H); 3.76(dd, 1H); 4.15(t, 1H); 4.25(s, 2H); 4.75(m, 1H); 7.33(s, 1H); 7.42(dd, 1H); 7.60(t, 1H); 7.71(dd, 1H); 7.93(s, 1H); 8.21 (brt, 1H); 8.52(s, 1H).
2 MS(ESP) 446(MH$^+$) for $C_{19}H_{20}FN_7O_3S$ NMR (CDCl$_3$) δ: 2.03(s, 3H); 3.60(s, 3H); 3.68(dd, 1H); 3.82(dd, 2H); 4.07(t, 1H); 4.82 (m, 1H); 5.42(s, 2H); 6.13(brt, 1H); 7.26(dd, 1H); 7.34(t, 1H); 7.36(s, 1H); 7.67(dd, 1H); 7.72(t, 1H); 7.78(s, 1H).
3 Isolated ratio of S:N substitution 2:1 MS(ESP): 459(MH$^+$) for $C_{20}H_{19}FN_6O_4S$ NMR(DMSO-D6) δ: 1.81(s, 3H); 3.42(t, 2H); 3.76 (dd, 1H); 4.14(t, 1H); 4.34(s, 2H); 4.74(m, 1H); 6.09(d, 1H); 7.42(dd, 1H); 7.46(s, 1H); 7.63(t, 1H); 7.71(dd, 1H); 7.88(d, 1H); 7.94 (t, 1H); 8.21(brt, 1H).
4 MS(ESP): 459(MH$^+$) for $C_{20}H_{19}FN_6O_4S$ NMR (DMSO-D6) δ: 1.82(s, 3H); 3.41(t, 2H); 3.76(dd, 1H); 4.15(t, 1H); 4.74(m, 1H); 5.34(s, 2H); 5.95(d, 1H); 7.42(dd, 1H); 7.53(s, 1H); 7.65(t, 1H); 7.71(dd, 1H); 7.89(d, 1H); 7.98(s, 1H); 8.22(brt, 1H); 12.56(br, 1H).

EXAMPLE 12

N-[(5S)-3-(3-Fluoro-4-(4-(1-methylimidazole-2-sulfonylmethyl)imidazol-1-ylphenyl)-2-oxooxazolidin-5-ylmethyl]acetamide N-[(5S)-3-(3-Fluoro-4-(4-(1-methylimidazole-2-thiomethylimidazol-1-yl)phenyl)-2-oxooxazolidin-5-ylmethyl]acetamide (53 mg, 0.12 mM) was dissolved in dichloromethane (10 ml), m-chloroperbenzoic acid (50% strength, 83 mg, 0.24 mM) added, and the mixture stirred at ambient temperature for 17 hours. The mixture was diluted with an equal volume of dichloromethane, and washed with sufficent 5% aqueous sodium bicarbonate to remove all acids. The organic phase was dried over magnesium sulfate, evaporated, and the residue dissolved in dichloromethane and chromatographed on a 5 g silica Mega Bond Elut® column, eluting with a gradient increasing in polarity from 0 to 20% methanol in dichloromethane. Relevant fractions were combined and evaporated to give the title product (20 mg).

MS (ESP): 477 (MH$^+$) for $C_{20}H_{21}FN_6O_5S$; NMR (CDCl$_3$) δ: 2.03 (s, 3H); 3.69 (t, 2H); 3.73 (s, 3H); 3.86 (dd, 1H); 4.08 (t, 1H); 4.71 (s, 2H); 4.83 (m, 1H); 6.43 (brt, 1H); 6.97 (s, 1H); 7.14 (s, 1H); 7.19 (s, 1H); 7.28 (dd, 1H); 7.33 (t, 1H); 7.67 (s, 1H); 7.71 (dd, 1H).

EXAMPLE 13

N-[(5S)-3-(3-Fluoro-4-(4-(2-Furoyloxymethyl)imidazol-1-yl)phenyl)-2-oxooxazolidin-5-ylmethyl]acetamide N-[(5S)-3-(3-Fluoro-4-(4-hydroxymethylimidazol-1-yl)phenyl)-2-oxooxazolidin-5-yl-methyl]acetamide (174 mg, 0.5 mM) and furan-2-carboxylic acid (168 mg, 1.5 mM) were suspended in dry dichloromethane (20 ml) under argon, and N,N-dimethylformamide dineopentyl acetal (462 mg, 2 mM) added. The mixture was stirred at ambient temperature for 48 hours giving a solution. The mixture was diluted with an equal volume of dichworomethane, and washed with sufficent 5% aqueous sodium bicarbonate to remove all acids. The organic phase was dried over magnesium sulfate, evaporated, and the residue dissolved in dichloromethane and chromatographed on a 5 g silica Mega Bond Elut® column, eluting with a gradient increasing in polarity from 0 to 10% methanol in dichloromethane. Relevant fractions were combined and evaporated to give the title product (184 mg).

MS (ESP): 443 (MH$^+$) for $C_{21}H_{19}FN_4O_6$; NMR (DMSO-D6) δ: 1.82 (s, 3H); 3.42 (t, 2H); 3.77 (dd, 1H); 4.16 (t, 1H); 4.75 (m. 1H); 5.22 (s,2H); 6.67(dd, 1H); 7.31 (d, 1H); 7.40 (dd, 1H); 7.63 (s, 1H); 7.67 (t, 1H); 7.72 (dd, 1H); 7.94 (d, 1H); 8.02 (t, 1H); 8.23 (brt, 1H).

EXAMPLES 14–18

N-[(5S)-3-(3-Fluoro-4-(4-hydroxymethylimidazol-1-yl)phenyl)-2-oxooxazolidin-5-yl-methyl]acetamide (139 mg, 0.4 mM) and the listed carboxylic acid (0.5 mM) were suspended in dry dichloromethane (5 ml) under argon, and N,N-dimethylformamide dineopentyl acetal (185 mg, 0.8 mM) added. The mixture was stirred at ambient temperature for 48 hours giving a solution. The mixture was applied directly to a 10 g silica Mega Bond Elut® column, and eluted with a gradient increasing in polarity from 0 to 10% methanol in dichloromethane. Relevant fractions were combined and evaporated to give products.

| Example | Product | Starting material | Foot notes |
|---|---|---|---|
| 14 | | | 1 |
| 15 | | | 2 |
| 16 | | | 3 |
| 17 | | | 4 |
| 18 | | | 5 |

1 MS(ESP): 454(MH+) for $C_{22}H_{20}FN_5O_5$ NMR(DMSO-D6) δ: 1.82(s, 3H); 3.41(t, 2H); 3.78(dd, 1H); 4.16(t, 1H); 4.75(m, 1H); 5.31(s, 2H); 7.44(dd, 1H); 7.67(t, 1H); 7.69(s, 1H); 7.73(dd, 1H); 7.83(d, 2H); 8.02(s, 1H); 8.22(brt, 1H); 8.78(d, 2H).
2 Tetramethylguanidine(0.15 ml) added to give complete solution before final column. MS(ESP): 456(MH+) for $C_{22}H_{22}FN_5O_5$ NMR(DMSO-D6) δ: 1.82 (s, 3H); 3.41(t, 2H); 3.76(dd, 1H); 3.84(s, 3H); 4.15(t, 1H); 4.74(m, 1H); 5.14(s, 2H); 6.06(m, 1H); 6.82(m, 1H); 7.07(m, 1H); 7.43(dd, 1H); 7.59(s, 1H); 7.66(t, 1H); 7.72(dd, 1H); 7.92(s, 1H); 8.21(brt, 1H).
3 MS(ESP): 459(MH+) for $C_{21}H_{19}FN_4O_5S$ NMR(DMSO-D6) δ: 1.82(s, 3H); 3.44(t, 2H); 3.77(dd, 1H); 4.15(t, 1H); 4.78(m, 1H); 5.23(s, 2H); 7.19(t, 1H); 7.43(dd, 1H); 7.63(s, 1H); 7.67(t, 1H); 7.72(dd, 1H); 7.80(d, 1H); 7.93(d, 1H); 8.00(s, 1H); 8.22(brt, 1H).
4 Tetramethylguanidine(0.15 ml) added to give complete solution before final column. MS(ESP): 473(NH+) for $C_{22}H_{21}FN_4O_5S$ NMR(DMSO-D6) δ: 1.82(s, 3H); 3.41(t, 2H); 3.77(dd, 1H); 3.93(s, 2H); 4.15(t, 1H); 4.74(m, 1H); 5.05(s, 2H); 6.95(m, 2H); 7.38(m, 1H); 7.43(dd, 1H); 7.54(s, 1H); 7.64(t, 1H); 7.72(dd, 1H); 7.97(s, 1H); 8.21(brt, 1H).
5 MS(ESP): 455(MH+) for $C_{21}H_{19}FN_6O_5$ NMR(DMSO-D6) δ: 1.82(s, 3H); 3.42(t, 2H); 3.77(dd, 1H); 4.16(t, 1H); 4.74(m, 1H); 5.34(s, 2H); 7.43(dd, 1H); 7.67(t, 1H); 7.70(s, 1H); 7.77(dd, 1H); 8.02(s, 1H); 8.21(brt, 1H); 8.79(m, 1H); 8.87(d, 1H); 9.21(d, 1H).

EXAMPLE 19

N-[(5S)-3-(3-Fluoro-4-(4-(4-methyl-5-nitropyridin-2-ylaminomethylimidazol-1-yl)phenyl)-2-oxooxazolidin-5-ylmethyl]acetamide N-[(5 S)-3-(3-Fluoro-4-(4-aminomethylimidazol-1-yl)phenyl)-2-oxooxazolidin-5-yl-methyl]acetamide (80 mg, 0.23 mM), 2-chloro-4-methyl-5-nitropyridine (80 mg, 0.46 mM) and triethylamine (1 ml) in acetonitrile (4 ml) under argon, were refluxed for 17 hours. Solvent was evaporated, and the residue dissolved in dichloromethane and chromatographed on a 10 g silica Mega Bond Elut® column, eluting with a gradient increasing in polarity from 0 to 10% methanol in dichloromethane. Relevant fractions were combined and evaporated to give the title product (77 mg).

MS (ESP): 484 (MH+) for $C_{22}H_{22}FN_7O_5$; NMR (DMSO-D6) δ: 1.81 (s, 3H); 2.44 (s, 3H); 3.40 (t, 2H); 3.74 (dd, 1H); 4.13 (t, 1H); 4.48 (brd, 2H); 4.74 (m, 1H); 6.46 (s, 1l); 7.39 (s, 1H); 7.42 (dd, 1H); 7.61 (t, 1H); 7.70 (dd, 1H); 7.95 (s, 1H); 8.16 (brq, 1H); 8.20 (brt, 1H); 8.81 (s, 1H).

The intermediate for this compound was prepared as follows.

N-[(5 S)-3-(3-Fluoro-4-(4-azidomethylimidazol-1-yl)phenyl)-2-oxooxazolidin-5-yl-methyl]acetamide N-[(5 S)-3-(3-Fluoro-4-(4-hydroxymethylimidazol-1-yl)phenyl)-2-oxooxazolidin-5-yl-methyl]acetamide (1.74 g, 5 mM) was suspended in dry dichloromethane (60 ml), diphenylphosphoryl azide (2.47 g, 9 mM) and 1,8-diazabicyclo[5.4.0]undec-7-ene (1.82 g, 12 mM) added, and the mixture stirred under argon at ambient temperature for 48 hours. The resulting solution was columned on silica (75 g) through a sinter funnel, eluting with a gradient increasing in polarity from 0 to 10% methanol in dichloromethane. Relevant fractions were combined and evaporated to give the title product (1.76 g).

MS (ESP): 374 (MH$^+$) for $C_{16}H_{16}FN_7O_3$; NMR (DMSO-D6) δ: 1.83 (s, 3H); 3.42 (t, 2H); 3.78 (dd, 1H); 4.16 (t, 1H); 4.32 (s, 2H); 4.76 (m, 1H); 7.44 (dd, 1H); 7.58 (s, 1H); 7.67 (t, 1H); 7.72 (dd, 1H); 8.02 (s, 1H); 8.22 (brt, 1H).

N-[(5S)-3-(3-Fluoro-4-(4-aminomethylimidazol-1-yl)phenyl)-2-oxooxazolidin-5-yl-methyl]acetamide N-[(5S)-3-(3-Fluoro-4-(4-azidomethylimidazol-1-yl)phenyl)-2-oxooxazolidin-5-yl-methyl]acetamide (1.38 g, 3.67 mM) was dissolved in ethanol (60 ml), treated with Lindlar catalyst (5% Pd on $CaCO_3$ partially poisoned with lead, 650 mg), and stirred under an atmosphere of hydrogen under balloon pressure for 4 hours. After filtration through celite, solvent was evaporated to give the title product as a gum, pure enough for further work (1.3 g).

MS (ESP): 348 (MH$^+$) for $C_{16}H_{18}FN_5O_3$; NMR (DMSO-D6) δ: 1.82 (s, 3H); 3.40 (t, 2H); 3.62 (s, 2H); 3.76 (dd, 1H); 4.14 (t, 1H); 4.76 (m, 1H); 7.27 (s, 1H); 7.41 (dd, 1H); 7.61 (t, 1H); 7.69 (dd, 1H); 7.88 (s, 1H); 8.22 (brt, 1H).

EXAMPLES 20–24

N-[(5S)-3-(3-Fluoro-4-(4-aminomethylimidazol-1-yl)phenyl)-2-oxooxazolidin-5-yl-methyl]acetamide (104 mg, 0.3 mM), triethylamine (0.1 ml. 0.718 mM) and the listed chloroheterocycle (0.45 mM) were heated in N,N-dimethylacetamide (1 ml) at 100° for 17 hours. The residue was dissolved in dichloromethane (80 ml), washed with dilute aqueous sodium bicarbonate (2×20 ml), and dried over sodium sulfate. The filtered solution was chromatographed on a 10 g silica Mega Bond Elut® column, eluting with a gradient increasing in polarity from 0 to 10% methanol in dichloromethane. Relevant fractions were combined and evaporated to give product.

| Example | Product | Starting material | Footnotes |
|---|---|---|---|
| 20 | | | 1 |
| 21 | | | 2 |
| 22 | | | 3 |
| 23 | | | 4 |

| Example | Product | Starting material | Foot notes |
|---|---|---|---|
| 24 | (structure) | (structure) | 5 |

1 MS(ESP): 470(MH+) for C21H20FN7O5 NMR(DMSO-D6) δ: 1.82(s, 3H); 3.41(t, 2H); 3.76(dd, 1H); 4.15(t, 1H); 4.53(brs, 2H); 4.74(m, 1H); 6.65(d, 1H); 7.42(dd, 1H); 7.44(s, 1H); 7.63(t, 1H); 7.71(dd, 1H); 7.97(t, 1H); 8.10(dd, 1H); 8.22(brt, 1H); 8.43(brt, 1H); 8.92(d, 1H).
2 MS(ESP): 450(MH+) for C22H20FN7O3 NMR(DMSO-D6) δ: 1.82(s, 3H); 3.41(t, 2H); 3.75(dd, 1H); 4.13(t, 1H); 4.52(d, 2H); 4.75(m, 1H); 6.65(dd, 1H); 7.26(brt, 1H); 7.30(s, 1H); 7.40(dd, 1H); 7.61(t, 1H); 7.69(dd, 1H); 7.89(m, 1H); 7.92(m, 1H); 8.22(brt, 1H); 8.27(dd, 1H).
3 MS(ESP): 493(MH+) for C22H20F4N6O3 NMR(DMSO-D6) δ: 1.82(s, 3H); 3.41(t, 2H); 3.76(dd, 1H); 4.14(t, 1H); 4.44(d, 2H); 4.75(m, 1H); 6.66(dd, 1H); 7.38(s, 1H); 7.42(dd, 1H); 7.62(overlapping m, 3H); 7.71(dd, 1H); 7.95(s, 1H); 8.22(brt, 1H); 8.27(s, 1H).
4 Chromatography gradient from 0 to 20% methanol in dichloromethane. MS(ESP): 426(MH+) for C20H20FN7O3 NMR(DMSO-D6) δ: 1.82(s, 3H); 3.41 (t, 2H); 3.75(dd, 1H); 4.14(t, 1H); 4.40(d, 2H); 4.74(m, 1H); 6.56(t, 1H); 7.28(s, 1H); 7.32(brt, 1H); 7.41(dd, 1H); 7.61(t, 1H); 7.69(dd, 1H); 7.91(t, 1H); 8.21(brt, 1H); 8.26(d, 2H).
5 MS(ESP): 426(MH+) for C20H20FN7O3 NMR(CDCl3) δ: 2.03(s, 3H); 3.68(t, 2H); 3.85(dd, 1H); 4.08(t, 1H); 4.56(d, 2H); 4.82(m, 1H); 5.36(br, 1H); 6.29(brt, 1H); 7.17(s, 1H); 7.25(dd, 1H); 7.34(t, 1H); 7.68(dd, 1H); 7.71(s, 1H); 7.80(d, 1H); 7.97(s, 1H); 8.02(d, 1H).

EXAMPLE 25

N-[(5S)-3-(3-Fluoro-4-(4-benzimidazol-1-ylmethylimidazol-1-yl)phenyl)-2-oxooxazolidin-5-ylmethyl]acetamide N-[(5S)-3-(3-Fluoro-4-(4-hydroxymethylimidazol-1-yl)phenyl)-2-oxooxazolidin-5-yl-methyl]acetamide (104 mg, 0.3 mM) and benzimidazole (71 mg, 0.6 mM) were suspended in dry acetonitrile (6 ml) under argon, and NAN-dimethylformamide dineopentyl acetal (208 mg, 0.9 mM) added. The mixture was refluxed for 8 hours. Solvent was evaporated, and the residue dissolved in dichloromethane and chrornatographed on a 10 g silica Mega Bond Elut® column, eluting with a gradient increasing in polarity from 0 to 20% methanol in dichnoromethane. Relevant fractions were combined and evaporated to give the title product (50 mg).

MS (ESP): 449 (MH+) for C23H21FN6O3; NMR (DMSO-D6) δ: 1.82 (s, 3H); 3.41 (t, 2H); 3.76 (dd, 1H); 4.14 (t, 1H); 4.75 (m, 1H); 5.39 (s, 2H); 7.18 (m, 2H); 7.41 (dd, 1H); 7.60–7.75 (overlapping in, 5H); 7.94 (s, 1H); 8.21 (brt, 1H); 8.28 (s, 1H).

EXAMPLE 26

N-[(5S)3-(3-Fluoro-4-(4-(4-ethoxycarbonyl-1,2,3-triazol-1-yl)methylimidazol-1-yl)phenyl)-2-oxooxazolidin-5-ylmethyl]acetamide N-[(5S)-3-(3-Fluoro-4-(4-azidomethylimidazol-1-yl)phenyl )-2-oxooxazolidin-5-yl-methyl]acetamide (200 mg, 0.54 mM) and ethyl propiolate (79 mg, 0.81 mM) were dissolved in acetonitrile (10 ml) and heated under reflux for 3 hours. Further ethyl propio late (79 mg) was added, and heting continued for a total of 7 hours. Solvent was evaporated, the residue dissolved in the minimum volume of dichloromethane, and chromatographed on a 10 g silica Mega Bond Elut® column, eluting with a gradient increasing in polarity from 0 to 10% methanol in dichloromethane. Relevant fractions were combined and evaporated to give the title product (184 mg), containing about 10% of the 5-ethoxycarbonyl isomer.

MS (ESP): 472 (MH+) for C21H22FN7O5; NMR (DMSO-D6) δ: 1.28 (t, 3H); 1.82 (s, 3H); 3.42 (t, 2H); 3.77 (dd, 1H); 4.14 (t, 1H); 4.28 (q, 2H); 4.75 (m, 1H); 5.59 (s, 2H); 7.44 (dd, 1H); 7 .6 4 (overlapping m, 2H); 7.73 (dd, 1H); 8.00 (t, 1H); 8.22 (brt, 1H); 8.71 (s, 1H).

EXAMPLE 27

N-[(5S)-3-(3-Fluoro-4-(4-(4-aminocarbonyl-1,2,3-triazol-1-yl)methylimidazol-1-yl)phenyl)-2-oxooxazolidin-5-ylmethyl]acetamide N-[(5S)-3-(3-Fluoro-4-(4-(4-ethoxycarbonyl-1,2,3-triazol-1-yl)methylimidazol-1-yl)phenyl)-2-oxooxazolidin-5-ylmethyl]acetmide (64 mg, 0.14 mM) was dissolved in methanol (10 ml) and concentrated aqueous ammonia solution (5 ml) added. The mixture was allowed to stand at ambient temperature for 12 hours, then evaporated to dryness to give the title product (54 mg).

MS (ESP): 443 (MH+) for C19H19FN8O4; NMR (DMSO-D6) δ: 1.81 (s, 3H); 3.40 (t, 2H); 3.76 (dd, 1H); 4.15 (t, 1H); 4.74 (m, 1H); 5.56 (s, 2H); 7.40 (overlapping m, 2H); 7.64–7.80 (overlapping m, 4H); 8.00 (s, 1H); 8.21 (brt, 1H); 8.46 (s, 1H).

EXAMPLES 28–31

N-[(5S)-3-(3-Fluoro-4-(4-aminomethylimidazol-1-yl)phenyl)-2-oxooxazolidin-5-yl-methyl]acetamide (104 mg, 0.33 mM) was suspended in dry dichloromethane (5 ml) under argon. Triethylamine (0.1 ml, 0.72 mM) was added followed by the appropriate acyl or sulfonyl chloride (0.4 mM) and the mixture stirred at ambient temperature for 1 hour. The solution was chromatographed directly on a 10 g silica Mega Bond Elut® column, eluting with a gradient increasing in polarity from 0 to 10% methanol in dichloromethane. Relevant fractions were combined and evaporated, taken up in dichloromethane (50 ml), and washed with aqueous 5% sodium bicarbonate before drying over magnesium sulfate to give the products after evaporation.

| Example | Product | Starting material | Foot notes |
|---|---|---|---|
| 28 | (furan-2-carboxamide linked product) | furan-2-carbonyl chloride | 1 |
| 29 | (quinoxaline-2-carboxamide linked product) | quinoxaline-2-carbonyl chloride | 2 |
| 30 | (thiophene-2-sulfonamide linked product) | thiophene-2-sulfonyl chloride | 3 |
| 31 | (quinoline-8-sulfonamide linked product) | quinoline-8-sulfonyl chloride | 4 |

1 MS(ESP): 442(MH$^+$) for $C_{21}H_{20}FN_5O_5$ NMR(DMSO-D6) δ: 1.82(s, 3H); 3.41(t, 2H); 3.74(dd, 1H); 4.12(t, 1H); 4.36(d, 2H); 4.74(m, 1H); 6.59(dd, 1H); 7.13(d, 1H); 7.32(s, 1H); 7.41(dd, 1H); 7.62(t, 1H); 7.70(dd, 1H); 7.79(d, 1H); 7.92(d, 1H); 8.24(brt, 1H); ); 8.67(brt, 1H).
2 MS(ESP): 504(MH$^+$) for $C_{25}H_{22}FN_7O_4$ NMR(DMSO-D6) δ: 1.81(s, 3H); 3.40(t, 2H); 3.75(dd, 1H); 4.14(t, 1H); 4.53(d, 2H); 4.74(m, 1H); 7.41 (overlapping m, 2H); 7.63(t, 1H); 7.71(dd, 1H); 7.97(overlapping m, 3H); 8.19(overlapping m, 3H); 9.22(brt, 1H); 9.47(s, 1H)
3 MS(ESP): 494(MH$^+$) for $C_{20}H_{20}FN_5O_5S_2$ NMR(DMSO-D6) δ: 1.82(s, 3H); 3.41(t, 2H); 3.75(dd, 1H); 4.01(d, 2H); 4.15(t, 1H); 4.75(m, 1H); 7.12(dd, 1H); 7.24(s, 1H); 7.42(dd, 1H); 7.56(t overlapping m, 2H); 7.71(dd, 1H); 7.88(overlapping m, 2H); 8.22(overlapping m, 2H).
4 MS(ESP): 539(MH$^+$) for $C_{25}H_{23}FN_6O_5S$ NMR(DMSO-D6) δ: 1.83(s, 3H); 3.41(t, 2H); 3.75(dd, 1H); 4.03(d, 2H); 4.14(t, 1H); 4.75(m, 1H); 6.99(s, 1H); 7.14(overlapping m, 3H); 7.56(t, 1H); 7.68(overlapping m, 3H); 8.20(overlapping m, 3H); 8.48(dd, 1H); 9.02(m, 1H).

EXAMPLES 32–34

N-[(5S)-3-(3-Fluoro-4-(4-carboxyimidazol-1-yl)phenyl)-2-oxooxazolidin-5-ylmethyl]acetamide (181 mg, 0.5 mM) and the listed alcohol (1.5 mM) were suspended in dry acetonitrile (2 ml), and N,N-dimethylformamide dineopentyl acetal (347 mg, 1.5 mM) added. The mixture was heated with stirring at 80° for 17 hours, cooled, solvent evporated, the residue dissolved in dichloromethane (50 ml), and washed with sufficient aqueous sodium bicarbonate to remove acid. After drying (magnesium sulfate) and evaporation to a suitable volume, the solution was chromatographed on a 10 g silica Mega Bond Elut® colunt, eluting with a gradient increasing in polarity from 0 to 10% methanol in dichloromethane. Relevant fractions were combined and evaporated to give the products.

| Example | Product | Starting material | Foot notes |
|---|---|---|---|
| 32 | (furfuryl ester linked product) | furfuryl alcohol | 1 |

| Example | Product | Starting material | Footnotes |
|---------|---------|-------------------|-----------|
| 33 | [structure] | [structure] HO-CH2-thiophene | 2 |
| 34 | There is no Example 34 | | |

1 MS(ESP): 443(MH+) for $C_{21}H_{19}FN_4O_6$ NMR(DMSO-D6) δ: 1.82(s, 3H); 3.41(t, 2H); 3.77(dd, 1H); 4.15(t, 1H); 4.74(m, 1H); 5.25(s, 2H); 6.47(m, 1H); 6.57(d, 1H); 7.43(dd, 1H); 7.68(d, 1H); 7.69(t, 1H); 7.71(dd, 1H); 8.11(m, 1H); 8.21(brt, 1H); ); 8.25(d, 1H).
2 MS(ESP): 459(MH+) for $C_{21}H_{19}FN_4O_5S$ NMR (DMSO-D6) δ: 1.81(s, 3H); 3.41(t, 2H); 3.77(dd, 1H); 4.15(t, 1H); 4.74(m, 1H); 5.45(s, 2H); 7.02(dd, 1H); 7.22(d, 1H); 7.43(dd, 1H); 7.55(d, 1H); 7.71(t, 1H); 7.74(dd, 1H); 8.11(s, 1H); 8.21(brt, 1H); ); 8.25(s, 1H).

The intermediate for this compound was prepared as follows.
N-[(5S)-3-(3-Fluoro-4-(4-carboxyimidazol-1-yl)phenyl)-2-oxooxazolidin-5-ylmethyl]acetamide N-[(5S)-3-(3-Fluoro-4-(4-hydroxymethylimidazol-1-yl)phenyl)-2-oxooxazolidin-5-ylmethyl]acetamide (9.74 g, 28 mM) and triethylamine (28.3 g, 0.28 M) were stirred in dimethylsulfoxide (70 ml) under argon at ambient temperature. A solution of pyridine-sulfur trioxide complex (13.4 g, 84 mM) in dimethylsulfoxide (70 ml) was added dropwise over minutes, maintaining the temperature at ~20° C. Stirring was continued for a further 1 hour to give a solution of N-[(5S)-3-(3-fluoro-4-(4-aldehydoimidazol-1-yl)phenyl)-2-oxooxazolidin-5-ylmethyl]acetamide. This was treated with ice-water (70 ml) and then acidified gradually with phosphoric acid (85%, 49 g), with cooling. The resulting suspension was then stirred at 20°, and a solution of sodium chlorite (5.04 g, 56 mM) in water (70 ml) added dropwise over 2 hours, before finally stirring 18 hours at ambient temperature. After dilution with ice water (1.4 l), the mixture was stirred 1 hour, the resulting precipitate filtered, washed with water (2×50 ml) and dried to give title product (8.2 g).

MS (Negative ESP): 361 (MH$^{31}$) for $C_{16}H_{15}FN_4O_5$; NMR (DMSO-D6+TFA) δ: 1.82 (s, 3H); 3.41 (t, 2H); 3.77 (dd, 1H); 4.16 (t, 1H); 4.76 (m, 1H); 7.47 (dd, 1H); 7.74, 7.78 (t overlapping dd, 2H); 8.23 (t, 1H); 8.42 (s, 1H); 8.82 (s, 1H).

EXAMPLES 35–38

N-[(5S)-3-(3-Fluoro-4-(4-carboxyimidazol-1-yl)phenyl)-2-oxooxazolidin-5-ylmethyl]acetamide (181 mg, 0.5 mM), the listed alcohol (1 mM), 4-dimethylaminopyridine (30 mg, 0.25 mM) and dicyclohexylcarbodiimide (206 mg, 1 mM) were dissolved in N,N-dimeihylformamide (2 ml), and stirred under argon for 17 hours. The mixture was diluted with dichloromethane (20 ml), washed with aqueous sodium dihydrogen phosphate (2M, 10 ml) and water (10 ml). After drying (magnesium sulfate) and evaporation to a suitable volume, the solution was chromatographed on a 10 g silica Mega Bond Elut® column, eluting with a gradient increasing in polarity from 0 to 10% methanol in dichloromethane. Relevant fractions were combined and evaporated to give the products.

| Example | Product | Starting material | Footnotes |
|---------|---------|-------------------|-----------|
| 35 | [structure] | [benzodioxine-CH2OH structure] | 1 |
| 36 | [structure] | HO-CH2-thiophene | 2 |

| Example | Product | Starting material | Footnotes |
|---|---|---|---|
| 37 | (benzimidazol-2-ylmethyl ester structure) | 2-(hydroxymethyl)benzimidazole | 3 |
| 38 | (2-(pyridin-2-yl)ethyl ester structure) | 2-(2-hydroxyethyl)pyridine | 4 |

1 MS(ESP): 443(MH$^+$) for $C_{25}H_{23}FN_4O_7$ NMR(DMSO-D6) δ: 1.81(s, 3H); 3.41(t, 2H); 3.77(dd, 1H); 4.15(t overlapping m, 2H); 4.37–4.54(complex m, 4H); 4.75(m, 1H); 6.85(m, 4H); 7.45(dd, 1H); 7.71(t, 1H); 7.74(dd, 1H); 8.12(s, 1H); 8.21(brt, 1H); 8.28(s, 1H).

2 MS(ESP); 506(MH$^+$) for $C_{26}H_{24}FN_5O_5$ NMR(DMSO-D6) δ: 1.82(s, 3H); 3.09(t, 2H); 3.41(t, 2H); 3.77(dd, 1H); 4.16(t, 1H); 4.42(t, 2H); 4.75(m, 1H); 6.96(t, 1H); 7.05(t, 1H); 7.23(d, 1H); 7.27(d, 1H); 7.45(dd, 1H); 7.59(d, 1H); 7.72(t, 1H); 7.76(dd, 1H); 8.11(s, 1H); 8.19(s, 1H); 8.23(brt, 1H); 10.84(br, 1H).

3 After dilution of the reaction mixture with water and dichloromethane, the product precipitated, and was filtered and washed with acetone. MS(ESP): 493(MH$^+$) for $C_{24}H_{21}FN_6O_5$ NMR(DMSO-D6) δ: 1.82(s, 3H); 3.41(t, 2H); 3.77(dd, 1H); 4.15(t, 1H); 4.74(m, 1H); 6.47(s, 2H); 7.16(m, 2H); 7.42(dd, 1H); 7.52(m, 2H); 7.73(t, 1H); 7.75(dd, 1H); 8.16(s, 1H); 8.22(brt, 1H); 8.35(s, 1H); 12.57(br, 1H).

4 MS(ESP): 468(MH$^+$) for $C_{23}H_{22}FN_5O_5$ NMR(DMSO-D6) δ: 1.82(s, 3H); 3.13(t, 2H); 3.41(t, 2H); 3.76(dd, 1H); 4.16(t, 1H); 4.56(t, 2H); 4.75(m, 1H); 7.21(dd, 1H); 7.34(d, 1H); 7.45(dd, 1H); 7.70(overlapping m, 3H); 8.08(s, 1H); 8.14(s, 1H); 8.22(brt, 1H); 8.49(d, 1H).

EXAMPLE 39

N-[(5S)-3-(3-Fluoro-4-(4-(4-morpholinocarbonyl) imidazol-1-yl)phenyl-2-oxooxazolidin-5-ylmethyl] acetamide N-[(5S)-3-(3-Fluoro-4-(4-(4-nitrophenoxycarbonyl) imidazol-1-yl)phenyl)-2-oxooxazolidin-5-ylmethyl] acetamide (170 mg, 0.35 mM) was dissolved in dichloromethane (20 ml) and morpholine (61 mg, 0.7 mM) added. The mixture was stirred at ambient temperature for 17 hours, and the solution chromatographed on a 10 g silica Mega Bond Elut® column, eluting with a gradient increasing in polarity from 0 to 10% methanol in dichloromethane. Relevant fractions were combined and evaporated to give title product (114 mg).

MS (ESP): 432 (MH$^+$) for $C_{20}H_{22}FN_5O_5$;, NMR (DMSO-D6) δ: 1.82 (s, 3H); 3.40 (t, 2H); ~3.6 (v br, 2H); 3.61 (m, 4H); 3.77 (dd, 1H); ~4.1 (v br, 2H); 4.15 (t, 1H); 4.74 (m, 1H); 7.44 (dd, 1H); 7.72 (t, 1H); 7.74 (dd, 1H); 7.98 (s, 1H); 8.07 (s, 1H); 8.22 (brt, 1H).

The intermediate for this compound was prepared as follows.

N-[(5S)-3-(3-Fluoro-4-(4-(4-nitrophenoxycarbonyl) imidazol-1-yl)phenyl)-2-oxooxazolidin-5-ylmethyl] acetamide N-[(5S)-3-(3-Fluoro-4-(4-carboxyimidazol-1-yl)phenyl)-2-oxooxazolidin-5-ylmethyl]acetamide (181 mg, 0.5 mM), 4-nitrophenol (139 mg, 1 mM), dicyclohexylcarbodiimide (144 mg, 0.7 mM) and 4-dimethylaminopyridine (61 mg, 0.5 mM) were dissolved in N,N-dimethylformamide (2 ml). The mixture was stirred at ambient temperature for 17 hours, diluted with dichloromethane (20 ml), washed with 1M aqueous sodium dihydrogen phosphate (10 ml), water (2×10 ml), and dried over magnesium sulfate. After filtration and evaporation to a suitable volume, the solution was chromatographed on a 10 g silica Mega Bond Elut® column, eluting with a gradient increasing in polarity from 0 to 10% methanol in dichloromethane. Relevant fractions were combined and evaporated to give title product (210 mg).

MS (ESP): 484 (MH$^+$) for $C_{22}H_{18}FN_5O_7$; NMR (DMSO-D6) δ: 1.82 (s, 3H); 3.42 (t, 2H); 3.79 (dd, 1H); 4.18 (t, 1H); 4.77 (m, 1H); 7.48 (dd, 1H); 7.57 (d, 2H); 7.72 (t overlapping dd, 2H); 8.22 (brt, 1H); 8.25 (s, 1H); 8.32 (d, 2H); 8.59 (s, 1H).

EXAMPLES 40–42

N-[(5S)-3-(3-Fluoro-4-(4-(4-nitrophenoxycarbonyl) imidazol-1-yl)phenyl)-2-oxooxazolidin-5-ylmethyl] acetamide (193 mg, 0.4 mM) and triethylamine (50 mg, 0.5 mM) were dissolved in dichloromethane (10 ml) and the listed amine (0.5 mM) added. The mixture was stirred at ambient temperature for 17 hours, and the solution chromatographed on a 10 g silica Mega Bond Elut® column, eluting with a gradient increasing in polarity from 0 to 20% methanol in dichloromethane. Relevant fractions were combined and evaporated to give title products.

| Example | Product | Starting material | Footnotes |
|---------|---------|-------------------|-----------|
| 40 | (structure) | H₂N-CH₂CH₂-(2-pyridyl) | 1 |
| 41 | (structure) | H₂N-CH₂CH₂-(1-methylpyrrol-2-yl) | 2 |
| 42 | (structure) | (4-pyridyl)-CH₂-NH₂ | 3 |

1 MS(ESP): 467(MH⁺) for $C_{23}H_{23}FN_6O_4$ NMR(DMSO-D6) δ: 1.82(s, 3H); 2.97(t, 2H); 3.41(t, 2H); 3.61(q, 2H); 3.77(dd, 1H); 4.15(t, 1H); 4.76(m, 1H); 7.20(dd, 1H); 7.27(d, 1H); 7.44(dd, 1H); 7.70(t overlapping m, 3H); 7.96(s, 1H); 8.05(s, 1H); 8.16(brt, 1H); 8.22(brt, 1H); 8.49(d, 1H).

2 MS(ESP): 506(MH⁺) for $C_{23}H_{25}FN_6O_4$ NMR(DMSO-D6) δ: 1.82(s, 3H); 2.74(t, 2H); 3.41(t overlapping q, 4H); 3.52(s, 3H); 3.77(dd, 1H); 4.16(t, 1H); 4.75(m, 1H); 5.81(m, 1H); 5.85(m, 1H); 6.58(m, 1H); 7.44(dd, 1H); 7.71(t, 1H); 7.76(m, 1H); 7.96(s, 1H); 8.07(s, 1H); 8.14(brt, 1H); 8.22(brt, 1H).

3 Solvent was acetonitrile, and reaction heated at 80° for 4 hours MS(ESP): 506(MH⁺) for $C_{22}H_{21}FN_6O_4$ NMR(DMSO-D6) δ: 1.82(s, 3H); 3.42(t, 2H); 3.77(dd, 1H); 4.16(t, 1H); 4.45(d, 2H); 4.76(m, 1H); 7.26(d, 2H); 7.45(dd, 1H); 7.72(t, 1H); 7.76(dd, 1H); 8.03(d, 1H); 8.11(t, 1H); 8.22(brt, 1H); 8.45(d, 2H); 8.79(brt, 1H).

EXAMPLES 43–44

N-[(5S)-3-(3-Fluoro-4-(4-carboxyimidazol-1-yl)phenyl)-2-oxooxazolidin-5-yl-methyl]acetamide (145 mg, 0.4 mM), and 1-hydroxybenzotriazole (67 mg, 0.5 mM) were dissolved in N,N-dimethylformamide (2 ml) and treated with a solution of dicyclohexylcarbodiimide (124 mg, 0.6 mM) in dichloromethane (1 ml). The mixture was stirred at ambient temperature for 2 hours, and the appropriate amine (0.5 mM) added. After stirring for 18 hours, the mixture was diluted with dichloromethane (50 ml) and shaken with dilute aqueous sodium bicarbonate (20 ml). Product precipitated and was filtered off, and washed with dichloromethane and water to give products.

| Example | Product | Starting material | Footnotes |
|---------|---------|-------------------|-----------|
| 43 | (structure) | 2-aminothiazole | 1 |

| Example | Product | Starting material | Foot notes |
|---------|---------|-------------------|------------|
| 44 | | | 2 |

1 MS(ESP): 445(MH$^+$) for C$_{19}$H$_{17}$FN$_6$O$_4$S NMR (DMSO-D6) δ: 1.82(s, 3H); 3.42(t, 2H); 3.78(dd, 1H); 4.17(t, 1H); 4.76(m, 1H); 7.24(d, 1H); 7.51(overlapping m, 2H); 7.76(t overlapping dd, 2H); 8.22(s overlapping brt, 2H) 8.41(s, 1H); 11.67(br, 1H)
2 Product did not precipitate, so washed with dilute aqueous sodium bicarbonate (3 × 20 ml), and the dried solution chromatographed on a 10 mg silica Mega Bond Elut ® column, eluting with a gradient increasing in polarity from 0 to 10% methanol in dichloromethane. Relevant fractions were combined and evaporated to give product. MS(ESP): 506(MH$^+$) for C$_{21}$H$_{19}$FN$_6$O$_4$ NMR (DMSO-D6) δ: 1.82(s, 3H); 3.42(t, 2H); 3.79(dd, 1H); 4.18(t, 1H); 4.76(m, 1H); 7.21(dd, 1H); 7.47(dd, 1H); 7.76(t overlapping dd, 2H); 8.23(overlapping m, 5H); 9.00(d, 1H); 10.25(br, 1H).

EXAMPLES 45–47

N-[(5S)-3-(3-Fluoro-4-(4-carboxyimidazol-1-yl)phenyl)-2-oxooxazolidin-5-yl-methyl]acetamide (181 mg, 0.5 mM) and 1-hydroxybenzotriazole (81 mg, 0.6 mM) were dissolved in dry N,N-dimethylformamide (2 ml) and treated with 1-(3-dimethylaminopropyl)-3-ethylcarbodiimide methiodide (178 mg, 0.6 mM) in dichloromethane (1 ml). The mixture was stirred at ambient temperature for 2 hours, and the appropriate amine (0.5 mM) added. After stirring for 18 hours, the solvent was evaporated, and the residue stirred with a mixture of 5% aqueous sodium carbonate (2 ml), dichloromethane (5 ml) and water (3 ml). After partial evaporation to remove dichloromethane, products were filtered and washed with water (2×5 ml).

| Example | Product | Starting material | Foot notes |
|---------|---------|-------------------|------------|
| 45 | | | 1 |
| 46 | Chiral | | 2 |
| 47 | | | 3 |

1 MS(ESP): 459(MH$^+$) for C$_{20}$H$_{19}$FN$_6$O$_4$S NMR (DMSO-D6) δ: 1.81(s, 3H); 2.26(s, 3H); 3.42(t, 2H); 3.78(dd, 1H); 4.17(t, 1H); 4.76(m, 1H); 6.78(s, 1H); 7.47(dd, 1H); 7.74(t, 1H); 7.76(dd, 1H); 8.20, 8.22(s overlapping brt, 2H); 8.39(s, 1H); 11.57(brs, 1H).
2 MS(ESP): 439(MH$^+$) for C$_{21}$H$_{19}$FN$_6$O$_4$ NMR(DMSO-D6) δ: δ: 1.82(s, 3H); 3.43(t, 2H); 3.79(dd, 1H); 4.19(t, 1H); 4.76(m, 1H); 7.14(dd, 1H); 7.47 (dd, 1H); 7.77, 7.84(overlapping m, 3H); 8.21(s overlapping m, 3H); 8.31(s, 1H); 8.34(dd, 1H); 9.57(s, 1H).
3 Excess amine (2 mM) used. Crude purified by chromatography on a 10 g silica Mega Bond Elut ® column, eluting with a gradient increasing in polarity from 0 to 25% methanol in dichloromethane. Relevant fractions were combined and evaporated to give product. MS(ESP): 454(MH$^+$) for C$_{21}$H$_{20}$FN$_7$O$_4$ NMR(DMSO-D6) δ: 1.81(s, 3H); 3.42(t, 2H); 3.78(dd, 1H); 4.16(t, 1H); 4.76(m, 1H); 5.90(s, 2H); 6.18(d, 1H); 7.31(d, 1H); 7.38(t, 1H); 7.74, 7.84(overlapping m, 2H); 8.16(s, 1H); 8.21(s overlapping m, 2H); 9.07(s, 1H).

EXAMPLE 48

N-[(5S)-3-(3-Fluoro-4-(4-(6-acetamidopyridin-2-ylaminocarbonyl)imidazol-1-yl)phenyl)-2-oxooxazolidin-5-ylmethyl]acetamide

N-[(5S)-3-(3-Fluoro-4-(4-(6-aminopyridin-2-ylaminocarbonyl)imidazol-1-yl)phenyl)-2-oxooxazolidin-5-ylmethyl]acetamide (70 mg, 0.15 mM) was dissolved in pyridine (3 ml) and treated with acetic anhydride (0.5 ml). After standing 60 hours at ambient temperature, solvent was evaporated, and the residue triturated with water (10 ml). Filtration gave the title product (47 mg).

MS (ESP): 496 (MH$^+$) for $C_{23}H_{22}FN_7O_5$; NMR (DMSO-D6) δ: 1.82 (s, 3H); 2.07 (s, 3H); 3.42 (t, 2H); 3.78 (dd, 1H); 4.17 (t, 1H); 4.76 (m, 1H); 7.47 (dd, 1H); 7.79 (overlapping m, 5H); 8.20 (s, 1H); 8.23 (brt, 1H); 8.30 (s, 1H); 9.36 (s, 1H); 10.36 (s, 1H).

EXAMPLES 49–80

Examples 49–80 (summarised in the Table below) were prepared using the following procedure which employed a Zymark robotic system for multiple parallel synthesis. 1-Hydroxybenzotriazole ester of N-[(5S)-3-(3-fluoro-4-(4-carboxyimidazol-1-yl)phenyl)-2-oxooxazolidin-5-ylmethyl]acetamide N-[(5S)-3-(3-Fluoro-4-(4-carboxyimidazol-1-yl)phenyl)-2-oxooxazolidin-5-yl-methyl]acetamide (25 mM) was suspended in sieve dried N,N-dirnethylformrnamide (200 ml) and 1-hydroxybenzotriazole (30 mM) added, and the mixture cooled in an ice-bath. 1-(3-Dimethylaminopropyl)-3-ethylcarbodiimide methiodide (30 mM) was added in portions over 10 minutes, and the mixture left to warm to ambient temperature over 2.5 hours. Aliquots (4 ml) of the above stock solution were then added to the listed aminoheterocycle (0.5 mM); if the amine was as a salt, triethylamine (0.2 ml) was added prior to this addition. The mixture was then stirred at 25 for 24 hours, 55° for 12 hours, then at 25° for a further 12 hours. After dilution of samples with 5% aqueous sodium bicarbonate solution (3 ml), and stirring at 25° for 2 hours, products were filtered using a nylon filter cup and washed with an additional portion of sodium bicarbonate solution (3 ml) to give the listed products. Exceptions to this general work-up are given in the footnotes.

Compounds so prepared were characterised by the presence of the correct molecular ion for MH$^+$ in their electrospray mass spectra, and by their HPLC retention time, using the following system and elution parameters, and in some cases by NMR.

| | | |
|---|---|---|
| | Column HYPERSIL ODS | 5 m |
| | Flow rate | 1.0 ml/min |
| | Detector Wavelength | 2541 |
| | Solvent A | 1 mMol TFA/H$_2$O |
| | Solvent B | 1 mMol TFA/CH$_3$CN |

| Time | % Solvent A | % Solvent B |
|---|---|---|
| 0 | 95 | 5 |
| 3 | 95 | 5 |
| 17 | 5 | 95 |
| 18 | 95 | 5 |
| 20 | 95 | 5 |

| Example | Structure | Starting Material | HPLC RT | Mass Ion | Notes |
|---|---|---|---|---|---|
| 49 | 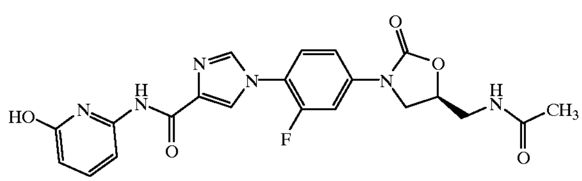 | | 8.74 | 455 | |
| 50 | 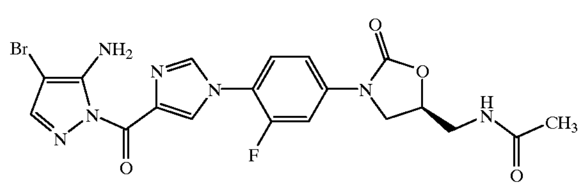 | | 10.01 | 506 | 1 |
| 51 | 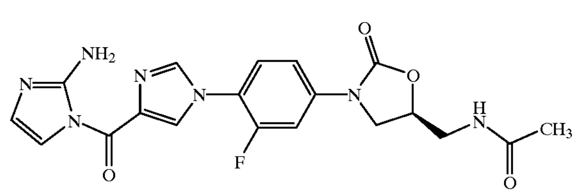 | | 8.95 | 428 | 2 |

-continued

| | | | | | |
|---|---|---|---|---|---|
| 52 | (structure) | (fragment) | 8.77 | | 3 |
| 53 | (structure) | (fragment) | 8.94 | 447 | 4 |
| 54 | (structure) | (fragment) | 9.06 | 489 | |
| 55 | (structure) | (fragment) HCl | 9.53 | 446 | 5 |
| 57 | (structure) | (fragment) | 9.71 | 478 | 6 |
| 58 | (structure) | (fragment) | 10.43 | 477 | 7 |
| 59 | (structure) | (fragment) | 9.76 | 478 | 8 |

-continued

| | | | | | |
|---|---|---|---|---|---|
| 60 | (structure) | (benzothiazol-2-amine) | 11.5 | 495 | 9 |
| 61 | (structure) | (5-aminouracil) | 8.71 | | 10 |
| 62 | (structure) | (4,6-dimethylpyridin-2-amine) | 9.61 | 467 | |
| 63 | (structure) | (5-bromopyridin-2-amine) | 11.74 | 517 | |
| 64 | (structure) | (5-methylpyridin-2-amine) | 9.37 | 453 | |
| 65 | (structure) | (pyridin-4-amine) | 8.84 | 439 | |
| 66 | (structure) | (quinolin-3-amine) | 9.74 | 489 | |

-continued

| 67 | | | 9.87 | 489 | |
| 68 | | | 11.62 | | 11 |
| 69 | | | 9.41 | 470 | 12 |
| 70 | | | 9.25 | 482 | |
| 71 | | | 8.80 | 444 | 13 |
| 72 | | | 9.74 | 459 | |

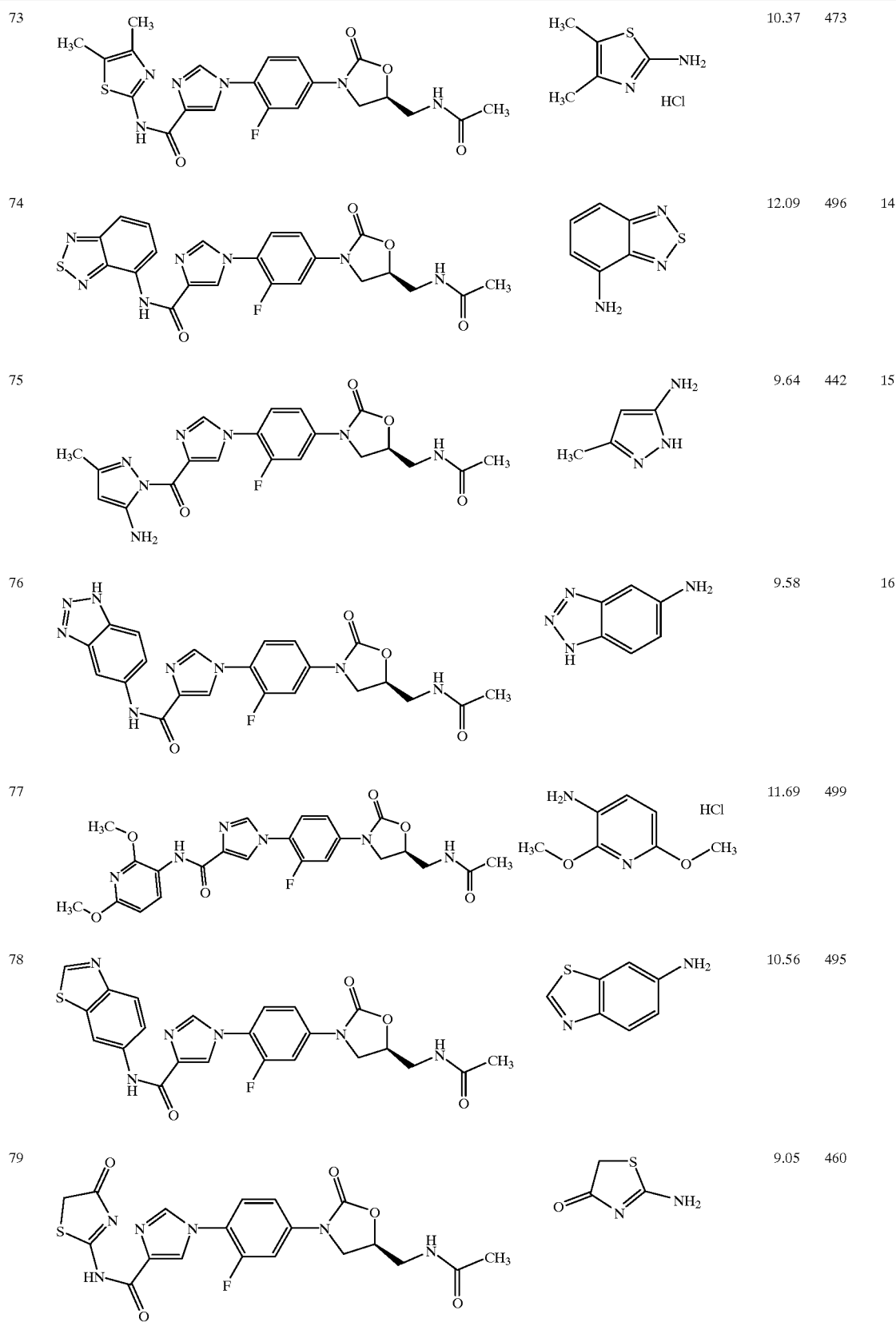

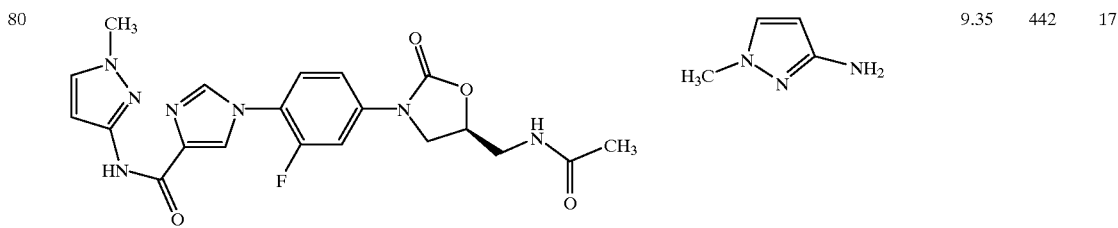

| | | | | |
|---|---|---|---|---|
| 80 | (structure) | | 9.35 | 442 | 17 |

1 NMR(DMSO-D6) δ: 1.82(s, 3H); 3.42(t, 2H); 3.78(dd, 1H); 4.19(t, 1H); 4.76(m, 1H); 5.78(s, 2H); 7.48(dd, 1H); 7.75(t, 1H); 7.78(dd, 1H); 8.21, 8.25(s overlapping t, 2H); 8.65(s, 2H).
2 NMR(DMSO-D6) δ: 1.82(s, 3H); 3.42(t, 2H); 3.78(dd, 1H); 4.17(t, 1H); 4.76(m, 1H); 6.51(d, 1H); 6.82(s, 2H); 7.47(dd, 1H); 7.77(dd, 1H); 7.79(t, 1H); 8.21(d, 1H); 8.24(t, 1H); 8.28(s, 1H); 8.53(s, 1H).
3 NMR(DMSO-D6) δ: 1.81(s, 3H); 3.42(t, 2H); 3.78(dd, 1H); 4.16(t, 1H); 4.77(m, 1H); 7.47(dd, 1H); 7.66(s, 3H); 7.78(t overlapping dd, 2H); 8.25(t, 1H); 8.27(s, 1H); 8.71(s, 1H).
4 NMR(DMSO-D6) δ: 1.82(s, 3H); 3.16(t, 2H); 3.40(t, 2H); 3.67(t, 2H); 3.78(dd, 1H); 4.16(t, 1H); 4.76(m, 1H); 7.44(dd, 1H); 7.72(t overlapping dd, 2H); 8.03(s, 1H); 8.06(s, 1H); 8.25(t, 1H).
5 After reaction mixture was diluted with 5% aqueous sodium bicarbonate solution (30 ml) to precipitate the product. NMR(DMSO-D6) δ: 1.82(s, 3H); 3.42(t, 2H); 3.78(dd, 1H); 4.17(t, 1H); 4.76(m, 1H); 7.47(dd, 1H); 7.75(t, 1H); 7.77(dd, 1H); 8.21(t, 1H); 8.23(s, 1H); 8.47(s, 1H); 9.16(s, 1H); 12.35(br, 1H).
6 NMR(DMSO-D6) δ: 1.81(s, 3H); 3.42(t, 2H); 3.78(dd, 1H); 4.17(t, 1H); 4.76(m, 1H); 7.03(dd, 2H); 7.42(dd, 2H); 7.45(dd, 1H); 7.74(t overlapping dd, 2H); 8.16(s, 1H); 8.22(t, 1H); 8.32(s, 1H).
7 NMR(DMSO-D6) δ: 1.82(s, 3H); 3.42(t, 2H); 3.79(dd, 1H); 4.17(t, 1H); 4.76(m, 1H); 6.37(d, 1H); 7.29(m, 2H); 7.42(d, 1H); 7.45(dd, 1H); 7.76(t, overlapping dd, 2H); 8.01(d, 1H); 8.13(s, 1H); 8.17(s, 1H); 8.24(t, 1H); 9.67(s, 1H); 11.05(brs, 1H).
8 NMR(DMSO-D6) δ: 1.81(s, 3H); 3.42(t, 2H); 3.78(dd, 1H); 4.16(t, 1H); 4.76(m, 1H); 7.47(overlapping m, 2H); 7.69(dd, 1H); 7.76(t overlapping dd, 2H); 8.01(s, 1H); 8.16(s, 1H); 8.19(d, 1H); 8.23(t, 1H); 8.26(s, 1H); 9.94(s, 1H).
9 NMR(DMSO-D6) δ: 1.81(s, 3H); 3.43(t, 2H); 3.78(dd, 1H); 4.16(t, 1H); 4.74(m, 1H); 7.13(t, 1H); 7.29(t, 1H); 7.46(d, 1H); 7.58(d, 1H); 7.78 (overlapping m, 3H); 8.11(s, 1H); 8.22(s, 1H); 8.25(t, 1H).
10 NMR(DMSO-D6) δ: 1.82(s, 3H); 3.40(t, 2H); 3.79(dd, 1H); 4.16(t, 1H); 4.75(m, 1H); 7.44(dd, 1H); 7.72(overlapping m, 2H); 8.05(t, 1H); 8.11(s, 1H); 8.22(s, 1H); 8.25(t, 1H); 9.07(t, 1H).
11 NMR(DMSO-D6) δ: 1.83(s, 3H); 3.42(t, 2H); 3.75(s, 3H); 3.79(dd, 1H); 4.16(t, 1H); 4.76(m, 1H); 6.84(dd, 1H); 7.32(d, 1H); 7.39(d, 1H); 7.46(dd, 1H); 7.73(t, 1H); 7.75(dd, 1H); 8.03(s, 2H); 8.24(t, 1H).
12 NMR(DMSO-D6) δ: 1.82(s, 3H); 1.99(s, 3H); 3.42(t, 2H); 3.78(dd, 1H); 4.16(t, 1H); 4.76(m, 1H); 5.46(s, 1H); 7.44(dd, 1H); 7.71(t, 1H); 7.74(dd, 1H); 7.93(s, 1H); 8.00(s, 1H); 8.27(t, 1H).
13 NMR(DMSO-D6) δ: 1.81(s, 3H); 3.42(t, 2H); 3.78(dd, 1H); 4.16(t, 1H); 4.74(s overlapping m, 2H); 6.64(brs, 2H); 7.41(dd, 1H); 7.66(t, 1H); 7.74 (dd, 1H); 8.12(s, 1H); 8.28(t, 1H); 8.69(s, 1H).
14 NMR(DMSO-D6) δ: 1.82(s, 3H); 3.44(t, 2H); 3.78(dd, 1H); 4.16(t, 1H); 4.76(m, 1H); 7.36(d, 1H); 7.46(dd, 1H); 7.75(overlapping m, 3H); 8.24(t, 1H); 8.27(s, 1H); 8.34(s, 1H); 8.48(dd, 1H); 10.28(br, 1H).
15 NMR(DMSO-D6) δ: 1.81(s, 3H); 2.06(s, 3H); 3.42(t, 2H); 3.79(dd, 1H); 4.17(t, 1H); 4.76(m, 1H); 5.23(s, 1H); 6.66(s, 2H); 7.47(dd, 1H); 7.75 (overlapping m, 2H); 8.18(s, 1H); 8.26(t, 1H); 8.68(dd, 1H).
16 NMR(DMSO-D6) δ: 1.83(s, 3H); 3.42(t, 2H); 3.79(dd, 1H); 4.16(t, 1H); 4.76(m, 1H); 7.23(dd, 1H); 7.45(dd, 1H); 7.54(d, 1H); 7.77(overlapping m, 2H); 8.13(m, 2H); 8.18(s, 1H); 8.27(t, 1H); 9.63(s, 1H).
17 NMR(DMSO-D6) δ: 1.82(s, 3H); 3.42(t, 2H); 3.66(s, 3H); 3.78(dd, 1H); 4.16(t, 1H); 4.76(m, 1H); 6.18(d, 1H); 7.29(d, 1H); 7.46(dd, 1H); 7.74(t overlapping m, 2H); 8.12(m, 1H); 8.14(s, 1H); 8.24(t, 1H).

EXAMPLES 81–82

N-[(5S)-3-(3-fluoro-4-(4-aldehydoimidazol-3-yl) phenyl)-2-oxooxazolidin-5-ylmethyl]acetamide (173 mg, 0.5 mM) was dissolved in N,N-dimethylformamide (4 ml) and the listed diamine (0.5 mM), followed by 2,3-dichloro-5,6-dicyano-1,4-benzoquinone (114 mg, 0.5 mM) added. The mixture was stirred at ambient temperature for 48 hours, then diluted with ethyl acetate (50 ml), and the precipitate filtered off. The filtrate was washed with water (50 ml), 2N sodium carbonate (50 ml), and brine (50 ml). After evporation the crude solid was dissolved in dichloromethane and chromatographed on a 10 g silica Mega Bond Elut® column, eluting with a gradient increasing in polarity from 0 to 12% methanol in dichloromethane. Relevant fractions were combined and evaporated to give products.

| Example | Product | Starting material | Foot notes |
|---|---|---|---|
| 81 | (structure) | (structure) | 1 |

-continued

| Example | Product | Starting material | Foot notes |
|---|---|---|---|
| 82 | 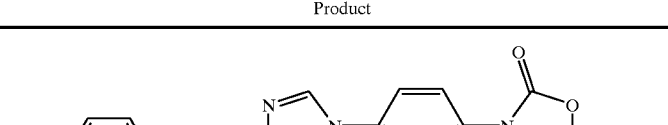 | 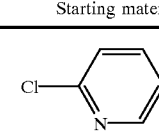 | 2 |

1 MS(ESP): 435(MH⁺) for $C_{22}H_{19}FN_6O_3$ NMR(DMSO-D6) δ: 1.82(s, 3H); 3.42(t, 2H); 3.79(dd, 1H); 4.14(t, 1H); 4.76(m, 1H); 7.13 (quintet, 2H); 7.46(tm, 2H); 7.55(m, 1H); 7.74(m, 1H); 7.78(t 1H); 8.19, 8.22(2 × s overlapping m, 3H); 12.67(s, 1H).
2 Work-up solvent was dichloromethane. MS(ESP): 449(MH⁺) for $C_{23}H_{21}FN_6O_3$ NMR(DMSO-D6) δ: 1.82(s, 3H); 3.43(t, 2H); 3.79 (dd, 1H); 4.17, 4.19(t overlapping s, 4H); 4.75(m, 1H); 7.20(quintet, 2H); 7.47(dd, 1H); 7.56(tm, 2H); 7.74(m, 1H); 7.79(t 1H); 8.22 (overlapping m, 3H).

EXAMPLES 83–84

Using an analagous technique to that of Examples 20–24, but using acetonitrile, and heating at reflux rather than 100°, the following compounds were prepared.

solution chromatographed on a 10 g silica Mega Bond Elut® column, eluting with a gradient increasing in polarity from 0 to 20% methanol in dichloromethane. Relevant fractions were combined and evaporated to give title product (52 mg).

| Example | Product | Starting material | Foot notes |
|---|---|---|---|
| 83 | 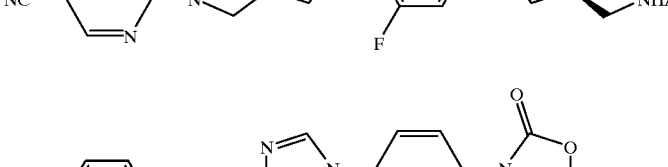 | | 1 |
| 84 | 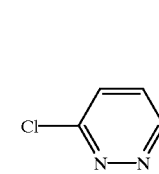 | | 2 |

1 MS(ESP): 450(MH⁺) for $C_{22}H_{20}FN_7O_3$ NMR(DMSO-D6) δ: 1.81(s, 3H); 3.40(t, 2H); 3.76(dd, 1H); 4.14(t, 1H); 4.44(d, 2H); 4.75(m, 1H); 6.63(d, 1H); 7.38, 7.41(s overlapping dd, 2H); 7.61(t, 1H); 7.68(overlapping m, 2H); 7.89(brt, 1H); 7.94(s, 1H); 8.20(brt, 1H); 8.38(d, 1H).
MS(ESP): 451(MH⁺) for $C_{21}H_{19}FN_8O_3$ NMR(DMSO-D6) δ: 1.81(s, 3H); 3.40(t, 2H); 3.76(dd, 1H); 4.14(t, 1H); 4.56(d, 2H); 4.74(m, 1H); 6.98(d, 1H); 7.42(dd, 1H); 7.45(s, 1H); 7.62(t, 1H); 7.70(overlapping m, 2H); 7.96(s, 1H); 8.16(br, 1H); 8.20(brt, 1H).

EXAMPLE 85

N-[(5S)-3-(3-Fluoro-4-(4-(N-(pyridin-2-yl)methyl-N-methylaminocarbonyl)-imidazol-1-yl)phenyl)-2-oxooxazolidin-5-ylmethyl]acetamide N-[(5S)-3-(3-fluoro-4-(4-(1-benzotriazolyloxy) carbonylimidazol-1-yl)phenyl)-2-oxooxazolidin-5-ylmethyl]acetamide (prepared as detailed for Exarnples 49–80; 243 mg, 0.5 mM) dissolved in DMF (4 ml) was treated with 2-(N-methylaminomethyl)pyridine (68 mg, 0.55mM). The mixture was stirred under nitrogen, and heated to 55° for 18 hours. After cooling, the mixture was diluted with saturated sodium bicarbonate solution (20 ml), extracted with ethyl acetate (2×10 ml), the extract washed with water and dried over magnesium sulfate. After evaporation the residue was dissolved in dichloromethane and the MS (ESP): 467 (MH⁺) for $C_{23}H_{23}FN_6O_4$; NMR (DMSO-D6) δ: 1.81 (s, 3H); 2.83 (brs, 1.5H); 3.42 (t, 2H); 3.47 (brs, 1.5H); 3.77 (dd, 1H); 4.15 (t, 1H); 4.74 (m, 2H); 5.40 (brs, 1H); 7.26 (m, 2H); 7.44 (d, 1H); 7.71 (overlapping m, 3H); 8.02 (s overlapping 2H); 8.21 (brt, 1H); 8.50 (d, 1H).

EXAMPLE 86

N-[(5S)-3-(3-Fluoro-4-(thiazol-2-ylimidazol-1-yl) phenyl)-2-oxoooxazolin-5-ylmethyl]acetamide N-[(5S)-3-(3-Fluoro-4-(thiocarbamidoimidazol-1-yl) phenyl)-2-oxooxazolidin-5-ylmethyl]acetamide (150 mg, 0.5mM) was dissolved in DMF (2 ml), and stirred under nitrogen with bromoacetaldehyde diethylacetal (200 mg, 1 mM) at 110° for 2 hours. After dilution with 5% sodium bicarbonate solution (20 ml), the mixture was extracted with dichloromethane (2×10 ml), the extract washed with water and dried over magnesium sulfate. After evaporation the reside was dissolved in dichloromethane and the solution chromatographed on a 10 g silica Mega Bond Elut® column, eluting with a gradient increasing in polarity from 0 ti 10% methanol in dichloromethane. Relevant fractions were combined and evaporated to give title product (41 mg).

MS (ESP) 402 (MH$^+$) for $C_{18}H_{16}FN_5O_3S$; NMR (DMSO-D6) δ: 1.83 (s, 3H); 3.42 (t, 2H); 3.78 (dd, 1H); 4.18 (t, 1H); 4.77 (m, 1H); 7.47 (dd, 1H); 7.63 (d, 1H); 7.77 (overlapping m, 2H); 7.82 (d, 1H); 8.08 (d, 1H); 8.13 (d, 1H); 8.22 (brt, 1H), The intermediate N-[(5S)-3-(3-fluoro-4-(4-thiocarbamidoimidazol-1-yl)phenyl)-2-oxooxazolidin-5-ylmethyl]acetamide was prepared as follows:

N-[(5S)-3-(3-Fluoro-4-(4-cyanoimidazol-1-yl)phenyl)-2-oxooxazolidin-5-ylmethyl]acetamide (WO97/31917; 686 mg, 2 mM) was dissolved in pyridine (30 ml), and triethylamine (1 ml, 7.2 mM) added. The mixture was stirred under a condenser cooled at −80°, and hydrogen sufide gas introduced throuigh a bubbler, until an excess was present, as judged by the appearance of liquid drops on the condenser. The mixture was stirred for 18 hours, the coolant in the condenser being allowed to evaporate. Excess by hydrogen sulfide was removed under mild vacuum, and the solution diluted with diethyl either (100 ml). The precipitate was filtered, washed with a little diethyl ether, then dichloromethane, to give the desired product as a solid (800 mg).

MS (CI): 378 (MH$^+$) for $C_{16}H_{16}FN_5O_3S$; NMR (DMSO-D6) δ: 1.83 (s, 3H); 3.42 (t, 2H); 3.78 (dd, 1H); 4.16 (t, 1H); 4.76 (m, 1H); 5 7.45 (dd. 1H); 7.74 (overlapping m, 2H); 8.07 (s, 1H); 8.11 (s, 1H); 8.22 (brt, 1H); 9.13 (brs, 1H); 9.48 (brs, 1H).

EXAMPLE 87

N-[(5S)-3-(3-Fluoro-4-(2-benzothiazolylaminocarbonylimidazol-1-yl)phenyl)-2-oxooxazolidin-5-ylmethyl]acetamide

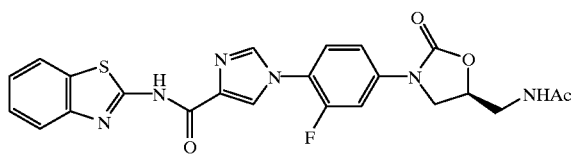

N-[(5S)-3-(3-Fluoro-4-(4-carboxyimidazol-1-yl)phenyl)-2-oxooxazolidin-5-ylmethyl]acetamide (1.81 g, 5 mM) and 1-hydroxybenzotriazole (0.81 g, 6 mM) were dissolved in DMF (40 ml) and stirred under nitrogen at ambient temperature. 1-(3-Dimethylaminopropyl)-3-ethylcarbodiimide methiodide (1.78 g, 6 mM) was added, and the mixture stirred at ambient temperature for 2 hours, before adding 2-aminobenzothiazole (0.75 g, 5 mM). After stirring for 5 days, the mixture was diluted slowly with saturated aqueous sodium bicarbonate solution (20 ml), then water added to 250 ml. The fine precipitate was filtered, and recrystallised from a mixture of acetic acid (30 ml) and water (20 ml) to give title product (1 g).

MS (ESP): 495 (MH$^+$) for $C_{23}H_{19}FN_6O_4S$; NMR (DMSO-D6) δ: 1.81 (s, 3H); 3.43 (t, 2H); 3.78 (dd, 1H); 4.14 (t, 1H); 4.77 (m, 1H); 7.31 (t, 1H); 7.31 (t, 1H); 7.49 (dd, 1H); 7.76 (overlapping m, 3H); 7.99 (d, 1H); 8.22 (brt, 1H); 8.24 (s, 1H); 8.51 (s, 1H); 11.98 (brs, 1H).

The compound shown in Example 60 is formed initially in this reaction, but rearranges to the product of Example 87 in the acidic conditions of the recrystallisation.

EXAMPLE 88

The following illustrate representative pharmaceutical dosage forms containing a compound of formula (I), or a pharmaceutically-acceptable salt thereof (hereafter compound X), for therapeutic or prophylactic use in humans:

| (a) | Tablet I | mg/tablet |
|---|---|---|
| | Compound X | 100 |
| | Lactose Ph.Eur | 179 |
| | Croscarmellose sodium | 12 |
| | Polyvinylpyrrolidone | 6 |
| | Magnesium stearate | 3 |
| (b) | Tablet II | mg/tablet |
| | Compound X | 50 |
| | Lactose Ph.Eur | 229 |
| | Croscarmellose sodium | 12 |
| | Polyvinylpyrrolidone | 6 |
| | Magnesium stearate | 3 |
| (c) | Tablet III | mg/tablet |
| | Compound X | 1 |
| | Lactose Ph.Eur | 92 |
| | Croscarmellose sodium | 4 |
| | Polyvinylpyrrolidone | 2 |
| | Magnesium stearate | 1 |
| (d) | Capsule | mg/capsule |
| | Compound X | 10 |
| | Lactose Ph.Eur | 389 |
| | Croscarmellose sodium | 100 |
| | Magnesium stearate | 1 |
| (e) | Injection I | (50 mg/ml) |
| | Compound X | 5.0% w/v |
| | Isotonic aqueous solution | to 100% |

Buffers, pharmaceutically-acceptable cosolvents such as polyethylene glycol, polypropylene glycol, glycerol or ethanol or complexing agents such as hydroxy-propyl β cyclodextrin may be used to aid formulation.

Note

The above formulations may be obtained by conventional procedures well known in the pharmaceutical art. The tablets (a)–(c) may be enteric coated by conventional means, for example to provide a coating of cellulose acetate phthalate.

What is claimed is:

1. A compound of formula (I),

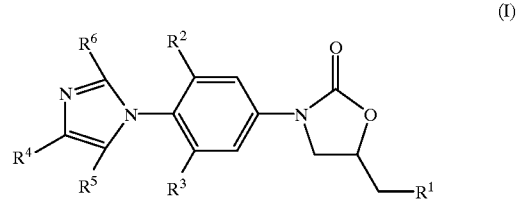

wherein $R^1$ is hydroxy, amino, chloro, fluoro, (1–4C) alkanesulfonyloxy, azido, (1–4C)alkoxy, or of the formula —NHC(═O)R$^a$ wherein R$^a$ is hydrogen, (1–4C) alkoxy, chloromethyl, dichloromethyl, cyanomethyl, methoxymethyl, acetylmethyl or (1–4C)alkyl;

$R^2$ and $R^3$ are independently hydrogen or fluoro;

$R^5$ and $R^6$ are independently selected from hydrogen, (1–4C)alkyl, halo and trifluoromethyl;

$R^4$ is —X—Y—HET;

wherein X is a direct bond or —CH(OH)— and Y is —(CH$_2$)$_m$—, —(CH$_2$)$_n$—NH—(CH$_2$)$_m$—, —CO—(CH$_2$)$_m$—, —CONH—(CH$_2$)$_m$—, —C(=S)NH—(CH$_2$)$_m$— or —C(=O)O—(CH$_2$)$_m$—;

or wherein X is —(CH$_2$)$_n$—, or —CH(Me)—(CH$_2$)$_m$— and Y is —(CH$_2$)$_m$—NH—(CH$_2$)$_m$—, —CO—(CH$_2$)$_m$—, —CONH—(CH$_2$)$_m$—, —C(=S)NH—(CH$_2$)$_m$—, —C(=O)O—(CH$_2$)$_m$— or —S(O)$_p$—(CH$_2$)$_m$—;

or wherein X is —CH$_2$O—, —CH$_2$NH— or —CH$_2$N(R)— wherein R is (1–4C)alkyl and Y is —CO—(CH$_2$)$_m$—, —CONH—(CH$_2$)$_m$— or —C(=S)NH—(CH$_2$)$_m$—; and additionally Y is —SO$_2$— when X is —CH$_2$NH— or —CH$_2$N(R)— wherein R (1–4C)alkyl, and Y is —(CH$_2$)$_m$— when X is —CH$_2$O— or —CH$_2$N(R)—, and Y is additionally —CON(R)—(CH$_2$)$_m$— wherein R is (1–4C)alkyl, when X is a direct bond;

wherein n is 1, 2 or 3; m is 0, 1, 2 or 3 and p is 0, 1 or 2; and when Y is —(CH$_2$)$_m$—NH—(CH$_2$)$_m$— each m is independently selected from 0, 1, 2 or 3;

wherein Het is a heterocyclic ring, which heterocyclic ring may be unsaturated, linked via either a ring carbon or ring nitrogen atom to —X—Y—, or saturated, linked via a ring nitrogen atom to —X—Y—, with the proviso that when it is unsaturated and linked via nitroen to —X—Y— the ring is not quaternised; which heterocyclic ring is optionally substituted on an available carbon atom by up to three substituents independently selected from (1–4C)alkyl, optionally substituted by trifluoromethyl, (1–4C)alkyl S(O)$_p$— wherein p is 0, 1 or 2, carbamoyl, N-(1–4C)alkylcarbamoyl, di(N-(1–4C)alkyl)carbamoyl, (1–4C)alkoxy, (1–4C) alkoxycarbonyl, cyano, nitro, amino, N-(1–4C) alkylamino, di(N-(1–4C)alkyl)amino or (1–4C) alkanoylamino, halo, trifluoromethyl, (1–4C)alkyl S(O)$_p$— wherein p is 0, 1 or 2, carboxy, (1–4C) alkoxycarbonyl, carbamoyl, N-(1–4C)alkylcarbamoyl, di(N-(1–4C)alkyl)carbamoyl, (2–4C)alkenyl, cyano, nitro, amino, imino, (2–4C)alkanoylamino, (1–4C) alkoxy, di(N-(1-4C)alkyl)aminomethylimino, hydroxy, oxo or thioxo (=S); and optionally substituted on an available nitrogen atom, if the ring will not thereby be quaternised, by (1–4C)alkyl optionally substituted by trifluoromethyl, (1–4C)alkyl S(O)$_p$— (wherein p is 0, 1 or 2), (1–4C)alkoxy, (1–4C) alkoxycarbonyl, carbamoyl, N-(1–4C)alkylcarbamoyl, di(N-(1–4C)alkyl)carbamoyl, cyano, nitro, amino, N-(1–4C)alkylamino, di(N-(1–4C)alkyl)amino or (1–4C)alkanoylamino, or oxo, to form an N-oxide; or pharmaceutically acceptable salts thereof.

2. A compound according to claim 1, wherein $R^1$ is acetamido; one of $R^2$ and $R^3$ is hydrogen and the other is fluoro; $R^5$ and $R^6$ are hydrogen; the —X—Y— link is —CH$_2$S—, —CH$_2$O—CO—, —CH$_2$NH—, —CH$_2$NHCO— or —CONH—; the Het. moiety in $R^4$ is a fully unsaturated aromatic ring linked via a ring carbon atom and selected from furan, pyrrole, thiophene, pyrazole, imidazole, pyridine, pyrimidine, pyrazine, pyridazine, 1,2,3- and 1,2,4-triazole, 1,2,4- and 1,3,4-thiadiazole, oxazole, isoxazole, oxazine, thiazole and isothiazole, indole, quinoline, isoquinoline, benzpyrrole, benzpyrazole, benzimidazole, quinoxaline, benzthiazole, benzoxazole, benzthiadiazole, benztriazole and 1,4-benzodioxan; wherein the Het moiety is optionally substituted by up to two substituents on an available carbon atom selected from (1–4C)alkyl, halo, cyano, nitro, amino, (2–4C) alkanoylamino, (1–4C)alkoxy, hydroxy, oxo and thioxo (=S), and optionally substituted by a substituent on an available nitrogen atom selected from (1–4C)alkyl and oxo; or pharmaccutically-acceptable salts thereof.

3. A compound according to claim 1, wherein the Het moiety is a monocyclic ring.

4. A compound according to claim 2, wherein the Het moiety is a monocyclic ring.

5. A compound selected from:

N-[(5S)-3-(3-Fluoro-4-(4-pyrimidin-2-ylthiomethylimidazol-1-yl)phenyl)-2-oxooxazolidin-5-ylmethyl]acetamide;

N-[(5S)-3-(3-Fluoro-4-(4-(2-furoyloxymethyl)imidazol-1-yl)phenyl)-2-oxooxazolidin-5-yl-methyl]acetamide;

N-[(5S)-3-(3-Fluoro-4-(4-(5-nitropyiidin-2-ylaminomethyl)imydazol-1-yl)phenyl)-2-oxooxazolidin-5-ylmethyl]acetamide;

N-[(5S)-3-(3-Fluoro-4-(4-(quinoxalin-2-ylcarbonylaminomethyl)imidazol-1-yl)phenyl)-2-oxooxazolidin-5-ylmethyl]acetamide;

N-[(5S )-3-(3-Fluoro-4-(4-(thiazol-2-ylaminocarbonyl) imidazol-1-yl)phenyl)-2-oxooxazolidin-5-ylmethyl] acetamide; and pharmaccutically-acceptable salts thereof.

6. A compound selected from:

N-[(5S)-3-(3-Fluoro-4-(4-(thiazol-2-ylaminocarbonyl) imidazol-1-yl)phenyl)-2-oxooxazolidin-5-ylmethyl] acetamide; and N-[(5S)-3-(3-Fluoro-4-(thiazol-2-ylimidazol-1-yl) phenyl)-2-oxooxazolidin-5-yl-methyl]acetamide; and pharmaceutically-acceptable salts thereof.

7. A pharmaceutical composition which comprises:

a compound according to claim 1; and a pharmaceutically acceptable diluent or carrier.

8. A pharmaceutical composition which comprises:

a compound according to claim 2; and a pharmaceutically acceptable diiuent or carrier.

9. A pharmaceutical composition which comprises:

a compound according to claim 3; and a pharmaceutically acceptable diluent or carrier.

10. A pharmaceutical composition which comprises:

a compound according to claim 4; and a pharmaceutically acceptable diluent or carrier.

11. A pharmaceutical composition which comprises:

a compound according to claim 5; and a pharmaceutically acceptable diluent or carrier.

12. A method for treating Gram-positive bacterial infections in a warm-blooded animal, in need of such treatment, which comprises administering to the animal an effective amount of a compound according to claim 1.

13. A method for treating Gram-positive bacterial infections in a warm-blooded animal, in need of such treatment, which comprises administering to the animal an effective amount of a compound according to claim 2.

14. A method for treating Gram-positive bacterial infections in a warm-blooded animal, in need of such treatment, which comprises administering to the animal an effective amount of a compound according to claim 3.

15. A method for treating Gram-positive bacterial infections in a warm-blooded animal, in need of such treatment, which comprises administering to the animal an effective amount of a compound according to claim 4.

16. A method for treating Gram-positive bacterial infections in a warm-blooded animal, in need of such treatment, which comprises administering to the animal an effective amount of a compound according to claim 5.

* * * * *